(12) United States Patent
Kowata et al.

(10) Patent No.: US 10,426,168 B2
(45) Date of Patent: *Oct. 1, 2019

(54) AGENT FOR CONTROLLING NOXIOUS ARTHROPODS

(71) Applicant: Sumitomo Chemical Company, Limited, Tokyo (JP)

(72) Inventors: Ayano Kowata, Takarazuka (JP); Kenichiro Awasaguchi, Takarazuka (JP); Kazuya Ujihara, Takarazuka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/736,348

(22) PCT Filed: Jun. 6, 2016

(86) PCT No.: PCT/JP2016/066713
§ 371 (c)(1),
(2) Date: Dec. 14, 2017

(87) PCT Pub. No.: WO2016/204006
PCT Pub. Date: Dec. 22, 2016

(65) Prior Publication Data
US 2018/0168159 A1    Jun. 21, 2018

(30) Foreign Application Priority Data

Jun. 17, 2015 (JP) .................. 2015-121744
Feb. 15, 2016 (JP) .................. 2016-025594

(51) Int. Cl.
*A01N 43/80* (2006.01)

(52) U.S. Cl.
CPC .................. *A01N 43/80* (2013.01)

(58) Field of Classification Search
CPC .................. A01N 43/80
See application file for complete search history.

(56) References Cited

U.S. PATENT DOCUMENTS

2015/0344466 A1   12/2015   Mitsudera et al.
2017/0295789 A1   10/2017   Mitsudera et al.

FOREIGN PATENT DOCUMENTS

| EP | 3178322 A1 | 6/2017 |
|---|---|---|
| JP | 2001348378 A | 12/2001 |
| JP | 2015051963 A | 3/2015 |
| JP | 2016030727 A | 3/2016 |
| WO | 2006138475 A2 | 12/2006 |
| WO | 2014119696 A1 | 8/2014 |
| WO | 2016017467 A1 | 2/2016 |
| WO | 2016040498 A1 | 3/2016 |

OTHER PUBLICATIONS

STN transcript excerpt (Year: 2015).*
STN search transcript section from search performed Nov. 23, 2018 (Year: 2018).*
Int'l Search Report dated Aug. 16, 2017 in Int'l Application No. PCT/JP2016/066713.
Int'l Preliminary Report on Patentability dated Dec. 19, 2017 in Int'l Application No. PCT/JP2016/066713.

* cited by examiner

*Primary Examiner* — Sarah Pihonak
*Assistant Examiner* — Jason Deck
(74) *Attorney, Agent, or Firm* — Panitch Schwarze Belisario & Nadel LLP

(57) ABSTRACT

An agent for controlling noxious arthropods has an exceptional noxious arthropod controlling effect, said agent containing an amide compound represented by Formula (I) and an inactive carrier. In formula (I), $R^2$ represents a C1-C3 chain hydrocarbon group, etc., $R^5$ and $R^6$ represent a hydrogen atom, etc., $R^9$ represents a C1-C4 alkyl group, etc., $R^{10}$ represents a C1-C4 alkyl group or hydrogen atom, etc., $R^{11}$ and $R^{12}$ each independently represent a C1-C4 alkyl group, etc., and Y represents a single bond, an oxygen atom, or $S(O)_u$; when Y is a single bond, m represents 0, and Q represents a C1-C8 chain hydrocarbon group, etc.; and when Y is an oxygen atom or $S(O)_u$, m represents any integer of 0 to 7, Q represents a C1-C8 chain hydrocarbon group, etc., a and b represent 0, 1, 2, or 3 (the sum of a and b representing any integer of 1 to 6), and u represents 0, 1, or 2.

1 Claim, No Drawings

AGENT FOR CONTROLLING NOXIOUS ARTHROPODS

CROSS-REFERENCE TO RELATED APPLICATION

This application is a Section 371 of International Application No. PCT/JP2016/066713, filed Jun. 6, 2016, which was published in the Japanese language on Dec. 22, 2016 under International Publication No. WO 2016/204006 A1, and claims priority under 35 U.S.C. § 119(b) to Japanese Patent Application No. 2015-121744, filed Jun. 17, 2015 and Japanese Patent Application No. 2016-025594, filed Feb. 15, 2016, the disclosures of which are incorporated herein by reference in their entireties.

TECHNICAL FIELD

The present invention relates to harmful arthropod control agent.

BACKGROUND ART

Heretofore, in order to control harmful arthropods, many compounds have been developed and come into practical use. Also, a certain class of amide compound has been known (see Patent Document 1).

CITATION LIST

Patent Literatures

Patent Literature 1: International Publication No. WO 2006/138475

SUMMARY OF INVENTION

Problems to be Solved by Invention

An object of the present invention is to provide an agent having an excellent efficacy for controlling harmful arthropods.

Means to Solve Problems

The present inventors have intensively studied to find an agent having an excellent efficacy for controlling harmful arthropods, and as a result, found that an agent comprising an amide compound represented by the below-mentioned formula (I) and inert carriers has an excellent efficacy for controlling harmful arthropods.

That is, the present invention includes the followings.
[1] An agent for controlling harmful arthropod, the agent comprising an amide compound represented by formula (I):

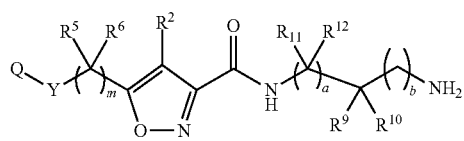

(I)

[wherein,
$R^2$ represents a C1-C3 chain hydrocarbon group which may have one or more substituents selected from a group consisting of hydroxy group and halogen atom, a hydrogen atom, a halogen atom, a cyano group or a formyl group,
$R^5$ and $R^6$ each independently represents a hydrogen atom, a halogen atom, a group represented by $R^3$, or a phenyl group which may have one or more substituents selected from Group A,
  $R^3$ represents a C1-C4 alkyl group which may have one or more halogen atom,
  $R^9$ represents a C1-C4 alkyl group which may have one or more fluorine atoms or a C1-C4 alkoxy group which may have one or more fluorine atoms,
  $R^{10}$ represents a C1-C4 alkyl group which may have one or more fluorine atoms, a C1-C4 alkoxy group which may have one or more fluorine atoms, or a hydrogen atom,
  $R^{11}$ represents a C1-C4 alkyl group which may have one or more fluorine atoms, a C1-C4 alkoxy group which may have one or more fluorine atoms, or a hydrogen atom,
  $R^{12}$ represents a C1-C4 alkyl group which may have one or more fluorine atoms, a C1-C4 alkoxy group which may have one or more fluorine atoms, or a hydrogen atom,
Y represents a single bond, an oxygen atom, or a $S(O)_u$,
  when Y represents a single bond, m is 0, and Q represents a C1-C8 chain hydrocarbon group which may have one or more substituents selected from. Group C,
  when Y represents an oxygen atom or a $S(O)_u$, m is an integer of any one of 0 to 7, and Q represents a C1-C8 chain hydrocarbon group which may have one or more substituents selected from Group C, or a substituent selected from Group B,
a and b is 0, 1, 2, or 3 {provided that the sum of a and b represents any one of an integer of 1 to 6},
u is 0, 1, or 2,
Group A: a group consisting of a C1-C4 chain hydrocarbon group which may have one or more halogen atoms, a C1-C4 alkyl group which may have one or more benzyloxy groups, $OR^3$ group, $S(O)_u R^3$ group, a carboxy group, $COOR^3$ group, $CONR^7R^8$ group, a phenyl group, a phenoxy group, a cyano group, a nitro group, a hydroxy group, a methoxymethyl group, and a halogen atom ($R^7$ and $R^8$ each independently represents a group represented by $R^3$, or a hydrogen atom),
Group B: a group consisting of a C3-C8 cycloalkyl group, an indanyl group, a 1,2,3,4-tetrahydronaphthyl group, a phenyl group, a naphthyl group, a pyridyl group, a quinolyl group, a furyl group, a thienyl group, a benzofuranyl group, a benzothienyl group, a 1,3-benzodioxolyl group, and a 1,4-benzodioxanyl group {provided that the C3-C8 cycloalkyl group, the indanyl group, the 1,2,3,4-tetrahydronaphthyl group, the phenyl group, the naphthyl group, the pyridyl group, the quinolyl group, the furyl group, the thienyl group, the benzofuranyl group, the benzothienyl group, the 1,3-benzodioxolyl group, and the 1,4-benzodioxanyl group may have one or more substituents selected from Group A},
Group C: a group consisting of a phenoxy group which may have one or more substituents selected from Group A, a substituent selected from Group B, a halogen atom, a carboxy group, $COOR^3$ group, $CONR^7R^8$ group, a cyano group, a nitro group, and a hydroxy group]
(hereinafter, referred to as "Present compound" or "Compound of the present invention") and an inert carrier.
[2] The agent for controlling harmful arthropod according to [1] wherein in the formula (I), $R^5$ and $R^6$ represent a hydrogen atom, Y represents an oxygen atom, m is 1, and Q represents a benzyl group or a naphthylmethyl group.
[3] The agent for controlling harmful arthropod according to [1] wherein Y in the formula (I), represents a single bond, m is 0, and Q represents a C1-C8 chain hydrocarbon group which may have one or more substituents selected from Group C.

[4] The agent for controlling harmful arthropod according to [3] wherein Q represents a C1-C8 chain hydrocarbon group.

[5] A method for controlling harmful arthropod, the method comprising applying a compound represented by formula (I):

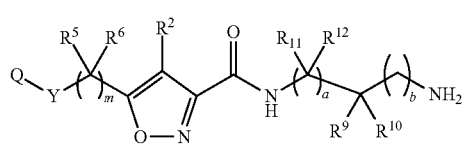

[wherein, $R^2$ represents a C1-C3 chain hydrocarbon group which may have one or more substituents selected from a group consisting of hydroxy group and halogen atom, a hydrogen atom, a halogen atom, a cyano group or a formyl group, $R^5$ and $R^6$ each independently represents a hydrogen atom, a halogen atom, a group represented by $R^3$, or a phenyl group which may have one or more substituents selected from Group A, $R^3$ represents a C1-C4 alkyl group which may have one or more halogen atom, $R^9$ represents a C1-C4 alkyl group which may have one or more fluorine atoms, $R^{10}$ represents a C1-C4 alkyl group which may have one or more fluorine atoms, or a hydrogen atom, $R^{11}$ represents a C1-C4 alkyl group which may have one or more fluorine atoms, a C1-C4 alkoxy group which may have one or more fluorine atoms, or a hydrogen atom, $R^{12}$ represents a C1-C4 alkyl group which may have one or more fluorine atoms, a C1-C4 alkoxy group which may have one or more fluorine atoms, or a hydrogen atom, Y represents a single bond, an oxygen atom, or a $S(O)_u$, when Y represents a single bond, m is 0, and Q represents a C1-C8 chain hydrocarbon group which may have one or more substituents selected from Group C, when Y represents an oxygen atom or a $S(O)_u$, m is an integer of any one of 0 to 7, and Q represents a C1-C8 chain hydrocarbon group which may have one or more substituents selected from Group C, or a substituent selected from Group B, a and b is 0, 1, 2, or 3 {provided that the sum of a and b represents any one of an integer of 1 to 6}, u is 0, 1, or 2, Group A: a group consisting of a C1-C4 chain hydrocarbon group which may have one or more halogen atoms, a C1-C4 alkyl group which may have one or more benzyloxy groups, $OR^3$ group, $S(O)_uR^3$ group, a carboxy group, $COOR^3$ group, $CONR^7R^8$ group, a phenyl group, a phenoxy group, a cyano group, a nitro group, a hydroxy group, a methoxymethyl group, and a halogen atom ($R^7$ and $R^8$ each independently represents a group represented by $R^3$, or a hydrogen atom), Group B: a group consisting of a C3-C8 cycloalkyl group, an indanyl group, a 1,2,3,4-tetrahydronaphthyl group, a phenyl group, a naphthyl group, a pyridyl group, a quinolyl group, a furyl group, a thienyl group, a benzofuranyl group, a benzothienyl group, a 1,3-benzodioxolyl group, and a 1,4-benzodioxanyl group {provided that the C3-C8 cycloalkyl group, the indanyl group, the 1,2,3,4-tetrahydronaphthyl group, the phenyl group, the naphthyl group, the pyridyl group, the quinolyl group, the furyl group, the thienyl group, the benzofuranyl group, the benzothienyl group, the 1,3-benzodioxolyl group, and the 1,4-benzodioxanyl group may have one or more substituents selected from Group A}, Group C: a group consisting of a phenoxy group which may have one or more substituents selected from Group A, a substituent selected from Group B, a halogen atom, a carboxy group, $COOR^3$ group, $CONR^7R^8$ group, a cyano group, a nitro group, and a hydroxy group]

to a harmful arthropod or a habitat where a harmful arthropod lives.

Effect of Invention

The control agent of the present invention has excellent control efficacies against harmful arthropods.

MODE FOR CARRYING OUT THE INVENTION

In the present compound, one or more stereoisomers may be existed. Examples of the stereoisomer include enantiomer, diastereomer, and geometric isomer, and the like. The present invention encompasses each stereoisomer, and mixtures containing the same in optional ratio thereof.

The present compound may form acid additional salts. Examples of an acid for forming the acid additional salts include inorganic acids such as hydrochloride, phosphoric acid and sulfuric acid, and organic acids such as acetic acid, trifluoroacetic acid, benzoic acid and p-toluene sulfonic acid. The acid additional salts may be obtained by mixing the present compound with one molar equivalent or more of an acid in solvent(s) and distilling the solvent(s) off.

The substituent to be used herein is explained.

The term of "halogen atom" to be used herein represents a fluorine atom, a chlorine atom, a bromine atom, or an iodine atom.

The phrase of "(which) may have one or more halogen atoms" represents that when two or more halogen atoms are present, these halogen atoms may be independently identical to or different from each other.

The phrase of "(which) may have one or more substituents" and "(which) has one or more substituents" represent that when two or more substituents are present, these substituents may be independently identical to or different from each other.

The expression of "CX-CY" to be used herein represent that the number of carbon atoms is from X to Y. For example, the expression of "C1-C4" represents that the number of carbon atoms is 1 to 4.

The term of "chain hydrocarbon group" represents an alkyl group, an alkenyl group, or an alkynyl group.

Examples of the term of "alkyl group" include a methyl group, an ethyl group, a propyl group, an isopropyl group, a 1,1-dimethylpropyl group, a 2,2-dimethylpropyl group, a 1,2-dimethylpropyl group, a 1-ethylpropyl group, a butyl group, a sec-butyl group, an isobutyl group, a tert-butyl group, a 1-methylbutyl group, a 2-methylbutyl group, a 3-methylbutyl group, a 1,1-dimethylbutyl group, a 2,2-dimethylbutyl group, a 3,3-dimethylbutyl group, a 1-ethylbutyl group, a 2-ethylbutyl group, a pentyl group, a 1-methylpentyl group, a 2-methylpentyl group, a 3-methylpentyl group, a 4-methylpentyl group, a hexyl group, a heptyl group, and an octyl group.

Examples of the term of "alkenyl group" include a vinyl group, a 1-propenyl group, a 2-propenyl group, a 1-methyl- 1-propenyl group, a 1-methyl-2-propenyl group, a 1,2-dimethyl-2-propenyl group, a 1,1-dimethyl-2-propenyl group, a 1-ethyl-1-propenyl group, a 1-ethyl-2-propenyl group, a 3-butenyl group, a 4-pentenyl group, a 5-hexenyl group, a 6-heptenyl group, and a 7-octenyl group.

Examples of the term of "alkynyl group" include an ethynyl group, a 1-propynyl group, a 2-propynyl group, a 1-methyl-2-propynyl group, a 1,1-dimethyl-2-propynyl group, a 1-ethyl-2-propynyl group, a 2-butynyl group, a 4-pentynyl group, a 5-hexynyl group, and a 7-octynyl group.

Examples of the phrase of "a C1-C4 chain hydrocarbon group which may have one or more halogen atoms" include a methyl group, a trifluoromethyl group, an allyl group, a 3,3-dichloro-2-propenyl group, and a 2-propenyl group.

Examples of the phrase of "a C1-C4 alkyl group which may have one or more halogen atom" include a methyl group, a trifluoromethyl group, a chlorodifluoromethyl group, a perfluoroisopropyl group, a butyl group, and a perfluorobutyl group.

Examples of the phrase of "C1-C4 alkyl group which may have one or more fluorine atoms" include a methyl group, an ethyl group, a propyl group, an isopropyl group, and a trifluoromethyl group.

Examples of the term of "C3-C8 cycloalkyl group" include a cyclopropyl group, a cyclobutyl group, a cyclopentyl group, a cyclohexyl group, and a cyclooctyl group.

Examples of the embodiment of the present compound to be used in the control agent of the present invention include the amide compounds described in the following embodiments.

Embodiment 1

An amide compound of the present invention wherein $R^2$ represents a methyl group or a hydrogen atom, $R^5$ and $R^6$ each independently represents, a hydrogen atom, a halogen atom or a group represented by $R^3$, $R^9$ represents a C1-C3 alkyl group, $R^{10}$, $R^{11}$ and $R^{12}$ each independently represents a hydrogen atom, a C1-C3 alkyl group, or a C1-C3 alkoxy group, and the sum of a and b is 1 to 3;

Embodiment 2

The amide compound described in Embodiment 1 wherein Y represents an oxygen atom and m is 0 or 1;

Embodiment 3

The amide compound described in Embodiment 2 wherein m is 1;

Embodiment 4

The amide compound described in Embodiment 3 wherein Q represents a C1-C8 chain hydrocarbon group which may have one or more substituents selected from Group C;

Embodiment 5

The amide compound described in Embodiment 3 wherein Q represents a C1-C8 alkyl group which may have one or more substituents selected from Group C;

Embodiment 6

The amide compound described in Embodiment 3 wherein Q represents a C1-C8 alkyl group which may have one or more halogen atoms;

Embodiment 7

The amide compound described in Embodiment 3 wherein Q represents a phenyl group which may have one or more substituents selected from Group A;

Embodiment 8

The amide compound described in Embodiment 3 wherein Q represents a C3-C8 cycloalkyl group which may have one or more substituents selected from Group A;

Embodiment 9

The amide compound described in Embodiment 3 wherein Q represents an indanyl group which may have one or more substituents selected from Group A;

Embodiment 10

The amide compound described in Embodiment 3 wherein Q represents a 1,2,3,4-tetrahydronaphthyl group which may have one or more substituents selected from Group A;

Embodiment 11

The amide compound described in Embodiment 3 wherein Q represents a naphthyl group which may have one or more substituents selected from Group A;

Embodiment 12

The amide compound described in Embodiment 3 wherein Q represents a pyridyl group which may have one or more substituents selected from Group A;

Embodiment 13

The amide compound described in Embodiment 3 wherein Q represents a quinolyl group which may have one or more substituents selected from Group A;

Embodiment 14

The amide compound described in Embodiment 3 wherein Q represents a furyl group which may have one or more substituents selected from Group A;

Embodiment 15

The amide compound described in Embodiment 3 wherein Q represents a thienyl group which may have one or more substituents selected from Group A;

Embodiment 16

The amide compound described in Embodiment 3 wherein Q represents a benzofuranyl group which may have one or more substituents selected from Group A;

Embodiment 17

The amide compound described in Embodiment 3 wherein Q represents a benzothienyl group which may have one or more substituents selected from Group A;

Embodiment 18

The amide compound described in Embodiment 3 wherein Q represents a 1,3-benzodioxolyl group which may have one or more substituents selected from Group A;

Embodiment 19

The amide compound described in Embodiment 3 wherein Q represents a 1,4-benzodioxanyl group which may have one or more substituents selected from Group A;

Embodiment 20

The amide compound described in Embodiment 1 wherein Y represents a single bond, m is 0, and Q represents a C1-C8 chain hydrocarbon group which may have one or more substituents selected from Group C;

Embodiment 21

The amide compound described in Embodiment 20 wherein Q represents a C1-C8 alkyl group which may have one or more substituents selected from Group C;

Embodiment 22

The amide compound described in Embodiment 20 wherein Q represents a C1-C8 alkyl group which may have one or more halogen atoms;

Embodiment 23

The amide compound described in any one of Embodiment 1 to Embodiment 22 wherein $R^5$ and $R^6$ represent a hydrogen atom;

Embodiment 24

The amide compound of the present invention wherein Y represents a single bond, m is 0, Q represents a C1-C8 alkyl group, $R^2$ represents a methyl group or a hydrogen atom, $R^5$ and $R^6$ represent a hydrogen atom, $R^9$ represents a C1-C3 alkyl group, $R^{10}$, $R^{11}$ and $R^{12}$ each independently represents a hydrogen atom or a C1-C3 alkyl group, a is 1, and b is 1;

Embodiment 25

The amide compound of the present invention wherein Y represents a single bond, m is 0, Q represents a C1-C8 alkyl group, $R^2$ represents a methyl group or a hydrogen atom, $R^5$ and $R^6$ represent a hydrogen atom, $R^9$ and $R^{10}$ represent a methyl group, $R^{11}$ and $R^{12}$ each independently represents a hydrogen atom or a C1-C3 alkyl group, a is 1, and b is 0;

Embodiment 26

The amide compound of the present invention wherein Y represents a single bond, m is 0, Q represents a C1-C8 alkyl group, $R^2$ represents a methyl group or a hydrogen atom, $R^5$ and $R^6$ represent a hydrogen atom, $R^9$ represents a methyl group, $R^{10}$ represents an ethyl group, $R^{11}$ and $R^{12}$ each independently represents a hydrogen atom or a C1-C3 alkyl group, a is 1, and b is 0;

Embodiment 27

The amide compound of the present invention wherein Y represents a single bond, m is 0, Q represents a C1-C8 alkyl group which may have one or more substituents selected from Group B, $R^2$ represents a methyl group or a hydrogen atom, $R^5$ and $R^6$ represent a hydrogen atom, $R^9$ represents a C1-C3 alkyl group, $R^{10}$, $R^{11}$ and $R^{12}$ each independently represents a hydrogen atom or a C1-C3 alkyl group, and the sum of a and b is any one of an integer of 1 to 3;

Embodiment 28

The amide compound of the present invention wherein Y represents an oxygen atom, m is 1, Q represents a methyl group which may have one or more substituents selected from Group B, $R^2$ represents a methyl group or a hydrogen atom, $R^5$ and $R^6$ represent a hydrogen atom, $R^9$ represents a C1-C3 alkyl group, $R^{10}$, $R^{11}$ and $R^{12}$ each independently represents a hydrogen atom or C1-C3 alkyl group, and the sum of a and b is any one of a integer of 1 to 3;

Embodiment 29

The amide compound of the present invention wherein $R^2$, $R^5$ and $R^6$ represent a hydrogen atom, $R^9$ represents a C1-C4 alkyl group, $R^{16}$ represents a C1-C4 alkyl group or a hydrogen atom, $R^{11}$ represents a C1-C4 alkyl group or a hydrogen atom, $R^{12}$ represents a C1-C4 alkyl group or a hydrogen atom, the sum of a and b is the integer of 1 or 2, Y represents an oxygen atom, m is 1, and Q represents a benzyl group or a naphthylmethyl group;

Embodiment 30

The amide compound of the present invention wherein $R^2$, $R^5$ and $R^6$ represent a hydrogen atom, $R^9$ represents a C1-C4 alkyl group, $R^{10}$ represents a C1-C4 alkyl group or a hydrogen atom, the sum of a and b is the integer of 1 or 2, Y represents a single bond, m is 0, and Q represents a C1-C8 alkyl group;

Embodiment 31

The amide compound of the present invention wherein $R^{11}$ represents a C1-C4 alkyl group which may have one or more fluorine atoms, or a C1-C4 alkoxy group which may have one or more fluorine atoms;

Embodiment 32

The amide compound of the present invention wherein $R^2$ represents a hydrogen atom or a methyl group, $R^5$ and $R^6$ represent a hydrogen atom, $R^9$ represents a C1-C4 alkyl group, $R^{10}$ represents a C1-C4 alkyl group, a C1-C4 alkoxy group, or a hydrogen atom, $R^{11}$ represents a C1-C4 alkyl group or a hydrogen atom, $R^{12}$ represents a C1-C4 alkyl group or a hydrogen atom, the sum of a and b is an integer of 1 or 2, Y represents an oxygen atom, m is 1, Q represents a methyl group which has a 1,2,3,4-tetrahydronaphthyl group, a phenyl group, or a 1,3-benzodioxolyl group (provided that the 1,2,3,4-tetrahydronaphthyl group, the phenyl group, and the 1,3-benzodioxolyl group may have one or more substituents selected from halogen atom, C1-C4 alkoxy group which may have one or more fluorine atoms, and C1-C4 alkyl group);

Embodiment 33

The amide compound of the present invention wherein $R^2$ represents a hydrogen atom or a methyl group, $R^5$ and $R^6$ represent a hydrogen atom, $R^9$ represents a C1-C4 alkyl group, $R^{10}$ represents a C1-C4 alkyl group, a C1-C4 alkoxy group, or a hydrogen atom, $R^{11}$ represents a C1-C4 alkyl group or a hydrogen atom, $R^{12}$ represents a C1-C4 alkyl group or a hydrogen atom, the sum of a and b is the integer of 1 or 2, Y represents an oxygen atom, m is 1, and Q represents a phenyl group or a pyridyl group (provided that the phenyl group and the pyridyl group may have one or more halogen atoms);

Embodiment 34

The amide compound of the present invention wherein $R^2$ represents a hydrogen atom or a methyl group, $R^5$ and $R^6$ represent a hydrogen atom, $R^9$ represents a C1-C4 alkyl group, $R^{10}$ represents a C1-C4 alkyl group, a C1-C4 alkoxy group or a hydrogen atom, $R^{11}$ represents a C1-C4 alkyl group or a hydrogen atom, $R^{12}$ represents a C1-C4 alkyl group or a hydrogen atom, the sum of a and b is the integer of 1 or 2, Y represents a single bond, m is 0, and Q represents a C1-C8 alkyl group which may have one or more substituents selected from the group consisting of C3-C8 cycloalkyl group, and phenyl group which may have one or more halogen atoms;

Embodiment 35

The amide compound of the present invention wherein $R^2$ represents a hydrogen atom or a methyl group, $R^5$ and $R^6$ represent a hydrogen atom, $R^9$ represents a C1-C4 alkyl group, $R^{10}$ represents a C1-C4 alkyl group, a C1-C4 alkoxy group, or a hydrogen atom, $R^{11}$ represents a C1-C4 alkyl group hydrogen atom, $R^{12}$ represents a C1-C4 alkyl group or a hydrogen atom, the sum of a and b is the integer of 1 or 2, Y represents a single bond, m is 0, and Q represents a C2-C8 alkyl group which may have halogen atom.

Next, the process of the present compound is explained.

The present compound may be prepared, for example, according to the below-mentioned process.
(Process 1)

The present compound may be prepared by reacting a compound represented by formula (A) (hereinafter, referred to as Compound (A)) and a compound represented by formula (B) (hereinafter, referred to as Compound (B)) in the presence of a base and a condensing agent.

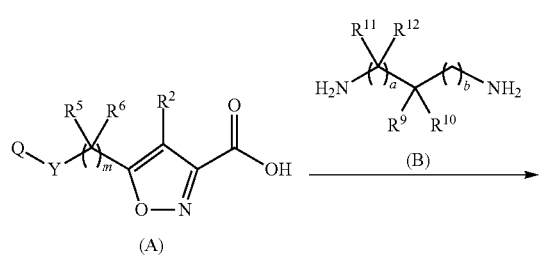

(A)

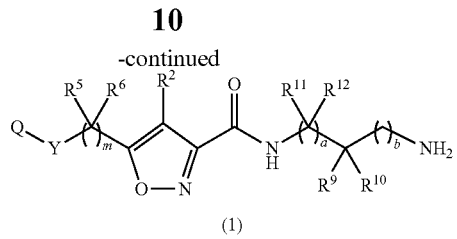

(1)

[wherein, the symbols are the same as defined above]

The reaction is usually carried out in a solvent. Examples of the solvent to be used in the reaction include hydrocarbons such as hexane, octane, toluene and xylene (hereinafter, collectively referred to as hydrocarbons), ethers such as diethyl ether, 1,4-dioxane, ethyleneglycol dimethyl ether, tert-butyl methyl ether and tetrahydrofuran (hereinafter, collectively referred to as ethers), halogenated hydrocarbons such as dichloromethane, chloroform, 1,2-dichloroethane and chlorobenzene (hereinafter, collectively referred to as halogenated hydrocarbons), acid amides such as dimethylformamide (hereinafter, referred to as DMF) (hereinafter, collectively referred to as acid amides), and esters such as ethyl acetate and butyl acetate (hereinafter, collectively referred to as esters).

Examples of the condensing agent include propyl phoshonic anhydride, dicyclohexyl carbodiimide, 1-ethyl-3-(3-dimethylaminopropyl)carbodiimide hydrochloride, 1H-benzotriazol-1-yloxytris(dimethylamino)phosphonium hexafluorophosphate, and (benzotriazol-1-yloxy)tripyrrolidinophosphonium hexafluorophosphate.

Examples of the base to be used in the reaction include alkali metal carbonates such as sodium carbonate and potassium carbonate (hereinafter, collectively referred to as alkali metal carbonates), and organic bases such as triethylamine, diisopropylethyamine, 1,8-diazabicyclo[5.4.0]undec-7-ene, 1,5-diazabicyclo[4.3.0]non-5-ene, pyridine, and 4-dimethylaminopyridine (hereinafter, collectively referred to as organic bases).

In the reaction, if necessary, 1-hydroxybenzotriazole, 1-hydroxy-7-azabenzotriazole, or N-hydroxysuccinimide and the like may be further added.

These compounds may be usually used within a range of 0.01 to 1 molar ratio(s), preferably within a range of 0.05 to 0.2 molar ratios, as opposed to 1 mole of the compound (A).

In the reaction, the compound (B) is usually used within a range of 1 to 10 molar ration(s), the condensing agent is usually used within a range of 1 to 5 molar ratio(s), and the base is usually used within a range of 1 to 10 molar ratio(s), as opposed to 1 mole of the compound (A).

The reaction period of the reaction is usually within a range of 5 minutes to 72 hours.

The reaction temperature of the reaction is usually within a range of −20° C. to 100° C.

When the reaction is completed, the reaction mixtures are extracted with organic solvents, and the resulting organic layers are worked up (for example, drying and concentration) to isolate the present compound.

Compound (A) may be prepared according to the similar method to those described in WO 2014/119696 A1.
(Process 2)

The present compound may be prepared by reacting a compound represented by formula (C) (hereinafter, referred to as Compound (C)) and Compound (B) in the presence of a base.

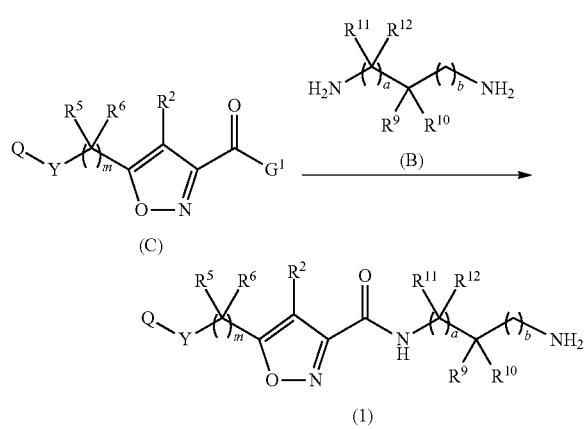

[wherein, G¹ represents a leaving group (for example, chlorine atom, or bromine atom), and the other symbols are the same as defined above.]

The reaction is usually carried out in a solvent. Examples of the solvents to be used in the reaction include the ethers, the hydrocarbons, the halogenated hydrocarbons, the esters, nitriles such as acetonitrile and butyronitrile (hereinafter, collectively referred to as nitriles) and mixtures thereof.

Examples of the bases to be used in the reaction include the alkali metal carbonates and the organic bases.

In the reaction, compound (B) is used usually within a range of 1 to 10 molar ratio(s), and the base is used usually with a range of 1 to 5 molar ratio(s), as opposed to 1 mole of Compound (C).

The reaction period of the reaction is within a range of 5 minutes to 72 hours.

The reaction temperature of the reaction is within a range of −20 to 100° C.

When the reaction is completed, the resulting reaction mixtures are extracted with organic solvents, and the resulting organic layers are worked up (for example, drying and concentration) to isolate the present compound.

Compound (C) may be prepared according to the similar method to those described in WO 2014/119696 A1.

(Process 3)

The present compound may be prepared by reacting a compound represented by formula (D) (hereinafter, referred to as Compound (D)) with an acid.

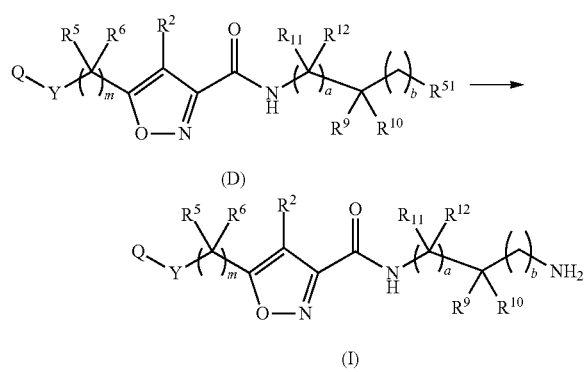

[wherein, R⁵¹ represents a tert-butoxycarbonylamino group, and the other symbols are the same as defined above.]

The reaction is usually carried out in a solvent. Examples of the solvent to be used in the reaction include the hydrocarbons, the halogenated hydrocarbons, and water.

Examples of the acid to be used in the reaction include hydrochloride, and trifluoroacetic acid.

In the reaction, the acid is usually used within the range of 1 to 100 molar ratio(s), as opposed to 1 mole of Compound (D).

The reaction period of the reaction is within the range of 5 minutes to 72 hours.

The reaction temperature of the reaction is within the range of −20 to 100° C.

When the reaction is completed, the resulting reaction mixtures are added to basic solutions (for example, aqueous sodium hydroxide solution), and the resulting reaction mixtures are extracted with organic solvents, and the resulting organic layers are worked up (for example, drying and concentration) to isolate the present compound.

Also, when the reaction is completed, the reaction mixtures are concentrated to take out the acid additional salt of the present compound.

Next, the process of an intermediate for preparing the present compound is explained.

(Reference Process 1)

Compound (D) may be prepared by reacting Compound (A) and a compound represented by formula (E) (hereinafter, referred to as Compound (E)) in the presence of a condensing agent.

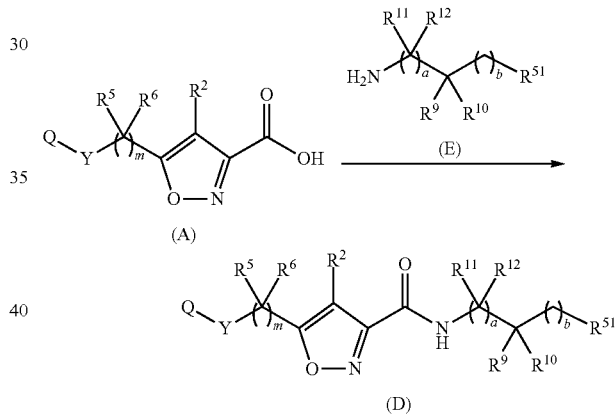

[wherein, the symbols are the same as defined above.]

The reaction may be conducted according to the similar method to those described in Process 1.

Compound (E) may be the publicly known compound, or may be prepared according to the similar method to the publicly known method.

(Reference Process 2)

Compound (D) may be prepared by reacting Compound (C) and Compound (E) in the presence of a base.

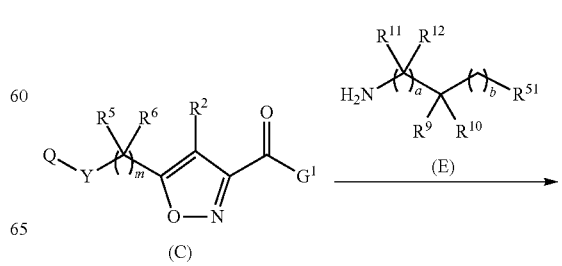

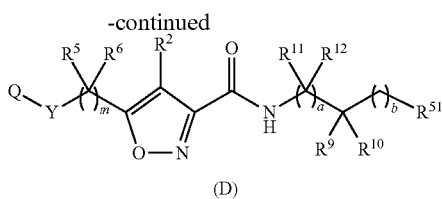

(D)

[wherein, the symbols are the same as defined above.]

The reaction may be conducted according to the similar method to those described in Process 2.

(Reference Process 3)

Compound (A) may be prepared also according to the below-mentioned scheme.

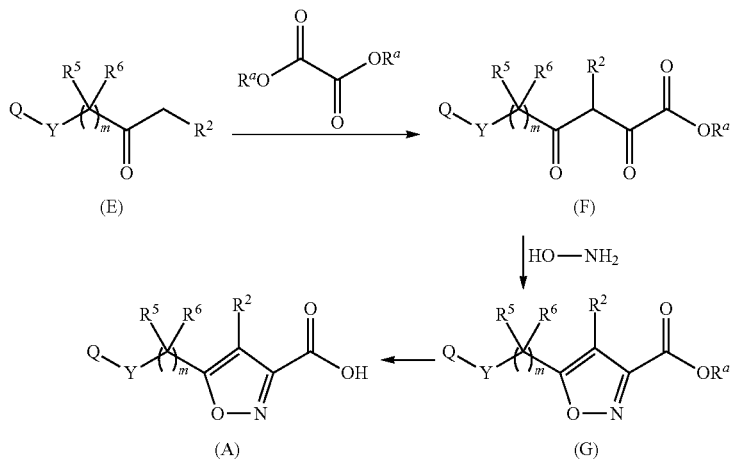

[wherein, $R^a$ represents a methyl group or an ethyl group, and the other symbols are the same as defined above.]

A compound represented by formula (F) may be prepared by reacting the compound (E) and an oxalic acid ester in the presence of a base. A compound represented by formula (G) may be prepared by reacting the compound represented by formula (F) and a hydroxylamine. Compound (A) may be prepared by hydrolyzing the compound represented by formula (G). These reactions may be conducted according to the similar methods to those described in, for example, Bioorganic & Medicinal Chemistry Letters, 23, 273-280 (2013).

Examples of harmful arthropods on which the control agent of the present invention has an efficacy include harmful insects and harmful mites. Specific examples of the harmful arthropods include the followings.

Hemiptera:

Delphacidae such as *Laodelphax striatellus, Nilaparvata lugens, Sogatella furcifera*, and *Peregrinus maidis;*

Cicadellidae such as *Nephotettix cincticeps, Nephotettix virescens, Nephotettix nigropictus* (Rice green leafhopper), *Recilia dorsalis, Empoasca onukii, Empoasca fabae, Dalbulus maidis, Mahanarva posticata* (Sugarcane froghopper), *Mahanarva fimbriolota* (Sugarcane root spittlebug), *Cofana spectra, Nephotettix nigropictus*, and *Recilia dorsalis;*

Aphididae such as *Aphis gossypii, Myzus persicae, Brevicoryne brassicae, Aphis spiraecola, Macrosiphum euphorbiae, Aulacorthum solani, Rhopalosiphum padi, Toxoptera citricidus, Hyalopterus pruni, Aphis glycines Matsumura, Rhopalosiphum maidis, Tetraneura nigriabdominalis, Viteus vitifoliae, Daktulosphaira vitifoliae* (Grape *Phylloxera*), *Phylloxera devastatrix Pergande* (Pecan *phylloxera*), *Phylloxera notabilis pergande* (Pecan leaf *phylloxera*), and *Phylloxera russellae Stoetzel* (Southern pecan leaf *phylloxera*);

Pentatomidae such as *Scotinophara lurida, Scotinophara coarctata* (Malayan rice black bug), *Nezara antennata, Eysarcoris parvus, Halyomorpha mista, Nezara viridula, Euschistus heros* (Brown stink bug), *Nezara viridula* (Southern green stink bug), *Piezodorus guildinii* (Red banded stink bug), *Scaptocoris castanea* (Burrower brown bug), *Oebalus pugnax*, and *Dichelops melacanthus;*

Alydidae such as *Riptortus clavetus, Leptocorisa chinensis, Leptocorisa acuta*, and *Leptocorisa* spp.;

Miridae such as *Trigonotylus caelestialium, Stenotus rubrovittatus, Lygus lineolaris*, and *Blissus leucopterus leucopterus* (Chinchi bug);

Aleyrodidae such as *Trialeurodes vaporariorum, Bemisia tabaci, Dialeurodes citri*, and *Aleurocanthus spiniferus;*

Coccidae such as *Aonidiella aurantii, Comstockaspis perniciosa, Unaspis citri, Ceroplastes rubens, Icerya purchasi, Planococcus kraunhiae, Pseudococcus longispinis, Pseudaulacaspis pentagona, Brevennia rehi*, and the like;

Psyllidae such as *Diaphorina citri, Psylla pyrisuga*, and *Bactericerca cockerelli;*

Tingitidae such as *Stephanitis nasi;*

Cimicidae such as *Cimex lectularius;*

*Quesada gigas* (Giant Cicada).

Lepidoptera:

Crambidae such as *Chilo suppressalis, Chilo polychrysus* (Darkheaded stm borer), *Tryporyza incertulas, Chilo polychrysus, Scirpophaga innotata, Scirpophaga incertula* (Yellow stem borer), *Sesamia inferens* (Pink borer), *Rupela albinella, Cnaphalocrocis medinalis, Marasmia patnalis, Marasmia exigna, Notarcha derogata, Plodia interpunctella, Plodia interpunctella, Ostrinia furnacalis, Hellula undalis, Pediasia teterrellus, Nymphula depunctalis, Marasmia* spp., *Hydraecia immanis* (Hop vine borer), *Ostrinia nubilalis* (European corn borer), *Elasmopalpus lignosellus* (Lesser cornstalk borer), *Epinotia aporema* (Bean Shoot Borer), *Diatraea saccharalis* (Sugarcane borer), and *Telchin licus* (Giant Sugarcane borer);

Noctuidae such as *Spodoptera litura, Spodoptera exigna, Pseudaletia separata, Mamestra brassicae, Sesamia inferens, Spodoptera mauritia, Spodoptera frugiperda, Spodoptera exempta, Agrotis Ipsilon, Plusia nigrisigna, Pseudoplusia includens* (Soybean looper), *Trichoplusia* spp., *Heliothis* spp. such as *Heliothis virescens, Helicoverpa* spp. such as

*Helicoverpa armigera*, *Anticarsia gammatalis* (Velvetbean caterpillar), and *Alabama argillacea* (Cotton leafworm);

Pieridae such as *Pieris rapae*;

Tortricidae such as *Adoxophyes* spp., *Grapholita molesta*, *Leguminivora glycinivorella*, *Matsumuraeses azukivora*, *Adoxophyes orana fasciata*, *Adoxophyes honmai*, *Homona magnanima*, *Archips fuscocupreanus*, *Cydia pomonella*;

Gracillariidae such as *Caloptilia theivora*, and *Phyllonorycter ringoniella*;

Cydia pomonellae such as *Carposina niponensis*, and *Ecdytolopha aurantiana* (Citrus fruit borer);

Lyonetiidae such as *Leucoptera coffeela* (Coffee Leaf miner), and *Lyonetia* spp., *Lymantria* spp., and *Euproctis* spp.;

Plutellidae such as *Plutella xylostella*;

Gelechiidae such as *Pectinophora gossypiella*, and *Phthorimaea operculella*;

Arctiidae such as *Hyphantria cunea*.
Thysanoptera;

Thripidae such as *Frankliniella occidentalis*, *Thrips parmi*, *Scirtothrips dorsalis*, *Thrips tabaci*, *Frankliniella intonsa*, *Frankliniella occidentalis*, *Haplothrips aculeatus*, and *Stenchaetothrips biformis*:
Diptera:

Culicidae such as *Culex pipiens pallens*, *Culex tritaeniorhynchus*, and *Culex quinquefasciatus*;

*Aedes* spp. such as *Aedes aegypti* and *Aedes albopictus*;

*Anopheles* spp. such as *Anopheles sinensis*;

Chironomidae;

Muscidae such as *Musca domestica* and *Muscina stabulans*;

Anthomyiidae such as *Delia platura*, *Delia antiqua*, and *Tetanops myopaeformis*;

Agromyzidae such as *Agromyza oryzae*, *Hydrellia griseola*, *Liriomyza sativae*, *Liriomyza trifolii*, and *Chromatomyia horticola*;

Chloropidae such as *Chlorops oryzae*;

Tephritidae such as *Dacus cucurbitae* and *Ceratitis capitata*;

Ephydridae such as *Hydrellia philippina* and *Hydrellia sasakii*;

Drosophilidae;

Phoridae such as *Megaselia spiracularis*;

Psychodidae such as *Clogmia albipunctata*;

Sciaridae;

Cecidomyiidae such as *Mayetiola destructor* and *Orseolia oryzae*;

Diopsidae such as *Diopsis macrophthalma*;

Tipulidae such as *Tipula oleracea* (Common cranefly) and *Tipula paludosa* (European cranefly).
Coleoptera:

Chrysomelidae such as *Diabrotica virgifera virgifera*, *Diabrotica undecimpunctata howardi*, *Diabrotica barberi*, *Diabrotica virgifera zeae*, *Diabrotica balteata LeConte*, *Diabrotica speciosa*, *Diabrotica specios* (Cucurbit Beetle), *Cerotoma trifurcata*, *Oulema melanopus*, *Aulacophora femoralis*, *Phyllotreta striolata*, *Leptinotarsa decemlineata*, *Oulema oryzae*, *Coiaspis brunnea*, *Chaetocnema pulicaria*, *Epitrix cucumeris*, *Dicladispa armigera*, *Stenolophus lecontei* (Seedcorn beetle), and *Clivinia impressifrons* (Slender seedcorn beetle);

Scarabaeidae such as *Anomala cuprea*, *Anomala rufocuprea*, *Popillia japonica*, *Rhizotrogus majalis* (European Chafer), *Bothynus gibbosus* (carrot beetle), *Colaspis brunnea* (Grape *Colaspis*), *Myochrous denticollis* (southern Corn leaf beetle), *Holotrichia* spp., and *Phyllophaga* spp. such as *Phyllophaga crinita*;

*Echinocnemus squameus* such as *Sitophilus zeamais*, *Echinocnemus squameus*, *Lissorhoptrus oryzophilus*, and *Sphenophorus venatus*;

Curculionidae such as *Anthonomus grandis*, *Sphenophorus callosus* (Southern Corn Billbug), *Sternechus subsignatus* (Soybean stalk weevil), and *Sphenophorus* spp. such as *Sphenophorus levis*;

Coccinellidae such as *Epilachna vigintioctopunctata*;

Bostrychidae such as *Lyctus brunneus* and *Tomicus piniperda*;

Bostrychidae;

Ptinidae;

Cerambycidae such as *Anoplophora malasiaca* and *Migdolus fryanus*;

*Agriotes* sp., *Aelous* sp., *Anchastus* sp., *Melanotus* sp., *Limonius* sp., *Conoderus* sp., or *Ctenicera* sp. such as *Melanotus okinawensis*, *Agriotes ogurae fuscicollis*, and *Melanotus legatus*;

Staphylinidae such as *Paederus fuscipes*; and

*Hypothenemus hampei* (Coffee Barry Borer).
Orthoptera:

Acrididae such as *Locusta migratoria*, *Gryllotalpa africana*, *Dociostaurus maroccanus*, *Chortoicetes terminifera*, *Nomadacris septemfasciata*, *Locustana pardalina* (Brown Locust), *Anacridium melanorhodon* (Tree Locust), *Calliptamus italicus* (Italian Locust), *Melanoplus differentialis* (Differential grasshopper), *Melanoplus bivittatus* (Twostriped grasshopper), *Melanoplus sanguinipes* (Migratory grasshopper), *Melanoplus femurrubrum* (Red-Legged grasshopper), *Camnula pellucida* (Clearwinged grasshopper), *Schistocerca gregaria*, *Gastrimargus musicus* (Yellow-winged locust), *Austracris guttulosa* (Spur-throated locust), *Oxya yezoensis*, *Oxya japonica*, and *Patanga succincta*;

Tettigoniidae such as *Acheta domesticus*, *Teleogryllus emma*, and *Anabrus simplex* (Mormon cricket).
Hymenoptera:

Tenthredinidae such as *Athalia rosae* and *Athalia japonica*;

*Solenopsis* spp.;

*Atta* spp. such as *Atta capiguara* (Brown leaf-cutting ant).
Blattodea:

Blattellidae such as *Blattella germanica*, *Periplaneta fuliginosa*, *Periplaneta americana*, *Periplaneta brunnea*, and *Blatta orientalis*.
Isoptera:

Termitidae such as *Reticulitermes speratus*, *Coptotermes formosanus*, *Incisitermes minor*, *Cryptotermes domesticus*, *Odontotermes formosanus*, *Neotermes koshunensis*, *Glyptotermes satsumensis*, *Glyptotermes nakajimai*, *Glyptotermes fuscus*, *Glyptotermes kodamai*, *Glyptotermes kushimensis*, *Hodotermopsis japonica*, *Coptotermes guangzhoensis*, *Reticulitermes amamianus*, *Reticulitermes miyatakei*, *Reticulitermes kanmonensis*, *Nasutitermes takasagoensis*, *Pericapritermes nitobei*, *Sinocapritermes mushae*, and *Cornitermes cumulans*.
Acari:

Tetranychidae such as *Tetranychus urticae*, *Tetranychus kanzawai*, *Panonychus citri*, *Panonychus ulmi*, *Oligonychus* spp., and *Brevipalpus phoenicis* such as Southern Turkey spider mites;

Eriophyidae such as *Aculops pelekassi*, *Phyllocoptruta citri*, *Aculops lycopersici*, *Calacarus carinatus*, *Acaphylla theavagrans*, *Eriophyes chibaensis*, and *Aculus schlechtendali*;

Tarsonemidae such as *Polyphagotarsonemus latus*;

Tenuipalpidae such as *Brevipalpus phoenicis*;

Tuckerellidae;

Ixodidae such as *Haemaphysalis longicornis, Haemaphysalis flava, Dermacentor taiwanicus, Dermacentor variabilis, Ixodes ovatus, Ixodes persulcatus, Ixodes scapularis, Amblyomma americanum, Boophilus microplus,* and *Rhipicephalus sanguineus;*

Acaridae such as *Tyrophagus putrescentiae* and *Tyrophagus similis;*

Pyroglyphidae such as *Dermatophagoides farinae* and *Dermatophagoides pteronyssinus.*

The agent for controlling harmful arthropod of the present invention comprises the present compound and inert carrier. The harmful arthrpod controlling agent of the present invention may be usually mixed with inert carrier such as solid carrier, liquid carrier and gaseous carrier, and if necessary, may be added by surfactants, and/or the other auxiliary agents for formulation, to formulate into emulsifiable concentrates, oil solutions, dusts, granules, wettable powders, flowables, microcapsules, aerosols, smoking agents, poison baits, resin formulations, shampoo formulations, pastes, foams, carbon dioxide gas formulations, tablets or the like. These formulations may be processed into mosquito coil, electric mosquito mat, electric mosquito liquid, smoking agent, fumigant, sheet, spot-on pesticide, or oral pesticide, and may be then used.

The harmful arthrpod controlling agent of the present invention can be used as a mixture with or together with other insecticides, miticides, nematocides, fungicides, plant growth regulators, herbicides, and synergists. In the preparing the formulations, the present compound may be used as itself or in a form of acid additional salts of the present compound. The agents for controlling harmful arthropod agent of the present invention usually contain 0.01 to 95% by weight of the present compound.

Examples of the solid carrier to be used in the formulation include fine powders or granules of clays (for example, kaolin clay, diatomaceous earth, bentonite, Fubasami clay, or acid white clay), synthetic hydrated silicon oxides, talcs, ceramics, other inorganic minerals (for example, sericite, quartz, sulfur, active carbon, calcium carbonate or hydrated silica) or chemical fertilizers (for example, ammonium sulfate, ammonium phosphate, ammonium nitrate, urea or ammonium chloride) and the others; as well as synthetic resins (for Example, polyester resins such as polypropylene, polyacrylonitrile, polymethylmethacrylate and polyethylene terephthalate; nylon resins (for Example, nylon-6, nylon-11 and nylon-66); polyamide resins; polyvinyl chloride, polyvinylidene chloride, vinyl chloride-propylene copolymers, and the others).

Examples of the above-mentioned liquid carriers include water; alcohols (for example, methanol, ethanol, isopropyl alcohol, butanol, hexanol, benzyl alcohol, ethylene glycol, propylene glycol or phenoxy ethanol); ketones (for example, acetone, methyl ethyl ketone or cyclohexanone); aromatic hydrocarbons (for example, toluene, xylene, ethyl benzene, dodecyl benzene, phenyl xylyl ethane or methylnaphthalene); aliphatic hydrocarbons (for example, hexane, cyclohexane, kerosene or light oil); esters (for example, ethyl acetate, butyl acetate, isopropyl myristate, ethyl cleate, diisopropyl adipate, diisobutyl adipate or propylene glycol monomethyl ether acetate); nitriles (for example, acetonitrile or isobutyronitrile); ethers (for example, diisopropyl ether, 1,4-dioxane, ethyleneglycol dimethyl ether, diethyleneglycol dimethyl ether, diethylene glycol monomethyl ether, propylene glycol monomethyl ether, dipropylene glycol monomethyl ether or 3-methoxy-3-methyl-1-butanol); acid amides; hydrogenated hydrocarbons; sulfoxides (for example, dimethyl sulfoxide); propylene carbonate; and vegetable oils (for example, soybean oil or cottonseed oil).

Examples of the above-mentioned gaseous carrier include fluorocarbon, butane gas, LPG (liquefied petroleum gas), dimethyl ether, and carbon dioxide gas.

Examples of the surfactants include nonionic surfactants such as polyoxyethylenated alkyl ethers, polyoxyethylenated alkyl aryl ethers and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), PAP (a mixture of monoisopropyl phosphate and diisopropyl phosphate), BHT (2,6-di-tert-butyl-4-methylphenol), and BHA (a mixture of 2-tert-butyl-4-methoxyphenol and 3-tert-butyl-4-methoxyphenol).

Examples of base material of the resin formulation include polyvinyl chloride polymers, polyurethane and the others, and a plasticizer such as phthalate esters (for example, dimethyl phthalate, dioctyl phthalate), adipic acid esters and stearic acid may be added to these base materials, if necessary. The resin formulation can be prepared by mixing the compound of the present invention with the above-mentioned base material, kneading the mixture, followed by molding it by injection molding, extrusion molding or pressure molding and the like. The resultant resin formulation can be subjected to further molding or cutting procedure and the like, if necessary, to be processed into shapes such as a plate, film, tape, net or string shape. These resin formulations can be processed into animal collars, animal ear tags, sheet products, trap strings, gardening supports and other products.

Examples of a base material for the poison baits include bait ingredients such as grain powder, vegetable oil, saccharide and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, insect attraction fragrances such as cheese flavor, onion flavor and peanut oil.

The method for controlling harmful arthropods of the present invention is conducted by applying an effective amount of the compound of the present invention to a harmful arthropod directly and/or a habitat thereof (for example, plant bodies, soil, an interior of a house, animal bodies). In the method for controlling harmful arthropods of the present invention, the Present compound is usually used in the form of the agent for controlling harmful arthropod of the present invention.

When the agent for controlling harmful arthropod of the present invention is used for controlling harmful arthropods in an agricultural field, the application dose as an amount of the present compound is usually within a range from 1 to 10,000 g per 10,000 m'. In the case where the agent for controlling harmful arthropod is formulated into the emulsifiable concentrate, the wettable powder, or the flowable formulation etc., the agent for controlling harmful arthropod of the present invention is usually applied by diluting it with water in such a way that a concentration of the present compound is within a range from 0.01 to 10, 000 ppm, and the granular formulation, or the dust formulation etc., is usually applied as itself without diluting it.

These formulations or an aqueous dilution thereof can be sparged directly to harmful arthropods or plants to be protected from harmful arthropods, and also may be applied to the soil of crop land in order to control harmful arthropods which live there.

The resin preparation which is processed into a sheet or a string may be applied by winding a plant with a sheet or a string of the resin preparation, putting a string of the resin preparation around a crop so that the plant is surrounded by the string, or laying a sheet of the resin preparation on the soil surface near the root of a plant.

When the agent for controlling harmful arthropods of the present invention is used to control harmful arthropods that live inside a house, the application dose of the Present compound is usually within a range from 0.01 to 1,000 mg per 1 m$^2$ of an area to be treated, in the case of using it on a planar area. In the case of using it spatially, the application dose of the Present compound is usually within a range from 0.01 to 500 mg per 1 m$^3$ of the space to be treated. When the agent for controlling harmful arthropods of the present invention is formulated into emulsifiable concentrates, wettable powders, flowables or the others, such formulations are usually applied after diluting it with water in such a way that a concentration of the present compound is within a range from 0.1 to 10,000 ppm, and then sparging it. In the case of being formulated into oil solutions, aerosols, smoking agents, poison baits and the others, such formulations are used as itself without diluting it.

When the agent for controlling harmful arthropods of the present invention is sued for controlling external parasites of livestock such as cows, horses, pigs, sheep, goats and chickens and small animals such as dogs, cats, rats and mice, the agent for controlling harmful arthropod of the present invention can be applied to the animals by a known method in the veterinary field. Specifically, when systemic control is intended, the agent for controlling harmful arthropod of the present invention is administered to the animals as a tablet, a mixture with feed or a suppository, or by injection (including intramuscular, subcutaneous, intravenous and intraperitoneal injections). On the other hand, when non-systemic control is intended, the agent for controlling harmful arthropod of the present invention is applied to the animals by means of spraying of the oil solution or aqueous solution, pour-on or spot-on treatment, or washing of the animal with a shampoo formulation, or by putting a collar or ear tag made of the resin formulations to the animal. In the case of administering to an animal body, the dose of the Present compound is usually within a range from 0.1 to 1,000 mg per 1 kg of an animal body weight.

EXAMPLES

Hereinafter, the present invention is explained in more detail by using Preparation Example, Formulation Example, and Test Example, however, the present invention should not be limited to these examples. Also, herein, Me represents methyl.

Preparation Example 1

5-{(Benzyloxy)methyl}isoxazol-3-carboxylic acid (0.50 g, 2.15 mmol) was dissolved in DMF (1.0 mL), and to the mixture was added 2-methylpropane-1,2-diamine (0.27 mL, 2.58 mmol), propyl phoshonic anhydride (50° ethyl acetate solution) (1.0 mL, 3.22 mmol) and diisopropyl ethylamine (1.2 mL, 6.44 mmol) at room temperature. The mixture was stirred at room temperature for 2 hours, and to the reaction mixture was added cold water, and the mixture was extracted with ethyl acetate twice. The organic layers were dried over anhydrous sodium sulfate, and filtered, and the filtrates were concentrated under reduced pressure. The residues were subjected to silica gel column chromatography to give 0.23 g of a compound represented by the following formula (1) (hereinafter, referred to as present compound (1)).

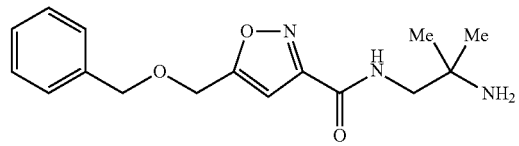

(1)

$^1$H-NMR (CDCl$_3$, TMS, δ (ppm)): 7.39-7.33 (5H, m), 6.73 (1H, s), 4.66 (2H, s), 4.61 (2H, s), 3.33 (2H, d), 1.17 (6H, s).

Preparation Example 2

5-[{Naphthalen-2-yl}methoxy]methyl]isoxazole-3-carboxylic acid (2.00 g, 7.1 mmol), 2-methylpropane-1,2-diamine (0.68 g, 8.1 mmol), 1-hydroxybenzotriazole (0.1 g, 0.7 mmol) and triethylamine (0.82 g, 8.1 mmol) were added to chloroform (30 mL). To the mixture solutions was added 1-ethyl-3-(3-dimethylaminopropyl)carbodiimide hydrochloride (1.35 g, 8.1 mmol) at room temperature, and the mixture was stirred at room temperature for two and a half hours. To the reaction mixture was 0.2 mol/L aqueous sodium hydroxide solution, and the mixture was extracted with ethyl acetate twice. The organic layers were washed with saturated brine, and the organic layers were dried over sodium sulfate, and filtered, and the filtrates were concentrated under reduced pressure. The residues were subjected to silica gel column chromatography to give 0.14 g of a compound represented by the following formula (2) (hereinafter, referred to as Present compound (2)).

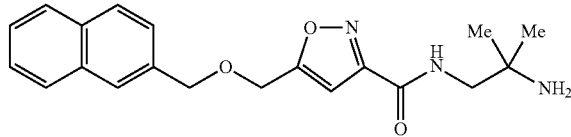

(2)

$^1$H-NMR (CDCl$_3$, TMS, δ (ppm)): 7.88-7.79 (4H, m), 7.52-7.46 (3H, m), 6.76 (1H, s), 4.77 (2H, s), 4.70-4.68 (2H, m), 3.33-3.32 (2H, m), 1.17 (6H, s).

Preparation Example 3

5-Butylisoxazole-3-carboxylic acid (hereinafter, referred to as Intermediate compound (1A)) (1.00 g, 5.91 mmol), 1-hydroxybenzotriazole (0.08 g, 0.59 mmol), and 2-methylpropane-1,2-diamine (0.62 g, 7.1 mmol) were dissolved into chloroform (10 mL). Then, thereto was added 1-ethyl-3-(3-dimethylaminopropyl)carbodiimide hydrochloride (1.35 g, 7.1 mmol), and the mixture was stirred at room temperature overnight. Thereafter, to the reaction mixture was added water, and the mixture was extracted with ethyl acetate twice. To the organic layers was added saturated brine, and the organic layers were separated with a separatory funnel, and the organic layers were dried over anhydrous sodium sulfate, and filtered, and the filtrates were concentrated under reduced pressure. The residues were subjected to silica gel column chromatography to give 0.71 g of a compound represented by the following formula (3) (hereinafter, referred to as Present compound (3)).

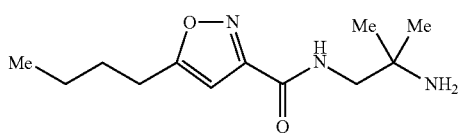

(3)

¹H-NMR (CDCl₃, TMS, δ (ppm)): 7.24 (1H, brs), 6.45-6.43 (1H, m), 3.32 (2H, d), 2.82-2.77 (2H, m), 1.75-1.66 (2H, m), 1.46-1.34 (4H, m), 1.17 (6H, s), 0.95 (3H, t).

Preparation Example 4

5-Butylisoxazole-3-carboxylic acid (0.22 g, 1.3 mmol) was dissolved into ethyl acetate (5 mL), and thereto was added DMF (0.02 g). To the mixture solution was added oxalyl chloride (about 0.5 mL) and the mixture was stirred at room temperature for 15 minutes, and concentrated under reduced pressure. To the resulting concentrates was added ethyl acetate (5 mL). The resulting solutions were added dropwise slowly under ice-cooling a solution of 2,3-dimethylbutane-2,3-diamine 2 hydrochloride salt (0.39 g, 2.1 mmol) in 1 mol/L aqueous sodium hydroxide solution (10 mL). The mixture was stirred vigorously at the same temperature for 1 hour, and to the reaction mixture was added water, and the mixture was extracted with ethyl acetate. The organic layer was extracted with 0.5 mol/L hydrochloric acid and the aqueous layers were adjusted with sodium hydroxide to make an alkaline solution, and the mixture was extracted with ethyl acetate twice. The resulting organic layers were washed with saturated brine, and the organic layers were dried over anhydrous sodium sulfate, and filtered, and the filtrates were concentrated under reduced pressure. The residues were subjected to silica gel column chromatography to give 0.01 g of a compound represented by the following formula (4) (hereinafter, referred to as Present compound (4)).

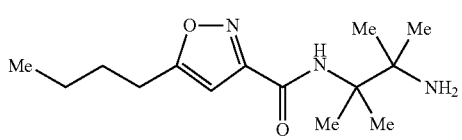

(4)

¹H-NMR (CDCl₃, TMS, δ (ppm)): 8.22 (1H, brs), 6.38 (1H, s), 2.80-2.74 (2H, m), 1.73-1.63 (2H, m), 1.55 (2H, s), 1.48 (6H, s), 1.44-1.33 (2H, s), 1.19 (6H, s), 0.93 (3H, t).

Preparation Example 5

To N-[3-{(tert-butoxycarbony)amino}-2,2-dimethylpropyl]-5-butylisoxazl-3-carboxamide which was prepared in Reference Preparation Example 1 (hereinafter, referred to as Intermediate compound (2)) (1.0 g, 2.89 mmol) was added trifluoroacetic acid (1.0 mL), and the mixture was stirred at room temperature for 30 minutes. To the reaction mixture was added chloroform, and the mixture was concentrated under reduced pressure to give 1.0 g of a compound represented by the following formula (5) (hereinafter, referred to as Present compound (5)) as a trifluoroacetate salt.

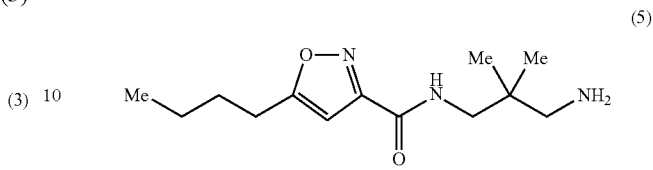

(5)

¹H-NMR (CDCl₃, TMS, δ (ppm)): 7.82-7.76 (2H, m), 7.50-7.46 (1H, m), 6.45 (1H, s), 5.45-5.32 (1H, m), 3.33 (2H, d), 2.82 (2H, t), 1.75-1.67 (2H, m), 1.41 (2H, td), 1.28 (2H, t), 1.14 (6H, s), 0.96 (3H, t).

Preparation Example 6

To Intermediate compound (2) (0.46 g, 1.30 mmol) was added concentrated hydrochloric acid (0.23 mL), and the mixture was stirred at room temperature for 2 hours. To the reaction mixture was added ethyl acetate, and the mixtures were concentrated under reduced pressure to give 470 mg of Present compound (5) as hydrochloride salt.

¹H-NMR (CDCl₃, TMS, δ (ppm)): 8.54-8.48 (3H, m), 7.51-7.47 (1H, m), 6.43 (1H, s), 3.41 (2H, d), 2.92-2.88 (2H, m), 2.78 (2H, t), 1.72-1.64 (2H, m), 1.44-1.34 (2H, m), 1.18 (6H, s), 0.94 (3H, t).

Preparation Example 7

Present compound (5) as hydrochloride salt (175 mg, 0.60 mmol) was dissolved into chloroform (2.0 mL), and thereto was aqueous saturated sodium carbonate solution (2.0 mL), and the mixture was stirred at room temperature for 2 hours. The reaction mixture was extracted with chloroform, and the organic layer was dried over anhydrous magnesium sulfate, and filtered, and the filtrates were concentrated under reduced pressure to give 138 mg of present compound (5)).

¹H-NMR (CDCl₃, TMS, δ (ppm)): 8.24-8.20 (1H, m), 6.43 (1H, s), 3.34 (2H, d), 2.78 (2H, t), 2.61 (2H, s), 1.74-1.64 (2H, m), 1.46-1.34 (2H, m), 1.42-1.22 (2H, m), 0.95 (6H, s), 0.94 (3H, t).

Preparation Example 8

A compound represented by the following formula (6) (hereinafter, referred to as Present compound (6)) 1.46 g was prepared by using 5-propylisoxazole-3-carboxylic acid in place of Intermediate compound (1A) according to the similar process to those described in Preparation Example 3.

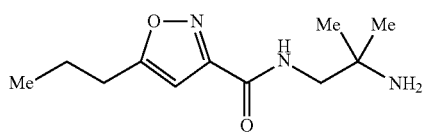

(6)

¹H-NMR (CDCl₃, TMS, δ (ppm)): 7.24 (1H, brs), 6.45-6.44 (1H, m), 3.33-3.29 (2H, m), 2.80-2.74 (2H, m), 1.80-1.70 (2H, m), 1.42 (2H, brs), 1.16 (6H, s), 1.00 (3H, t).

Preparation Example 9

5-[(2H-1,3-benzodioxazol-5-ylmethoxy)methyl]isoxazole-3-carboxylic acid (0.70 g, 2.53 mmol) was dissolved into dichloromethane (10 mL), and to the mixture were added 2-methylpropane-1,2-diamine (0.3 mL, 3.03 mmol), propyl phoshonic anhydride (50% ethyl acetate solution) (2.4 mL, 3.79 mmol) and diisopropylethylamine (1.3 mL, 7.58 mmol) at room temperature. The mixture was stirred at room temperature for 16 hours. To the reaction mixture was added cold water, and the mixture was extracted with ethyl acetate twice. The organic layers were washed with saturated brine, dried over anhydrous sodium sulfate, and filtered, and the filtrates were concentrated under reduced pressure. The residues were subjected to silica gel column chromatography to 0.41 g of a compound represented by the following formula (7) (hereinafter, referred to as Present compound (7)).

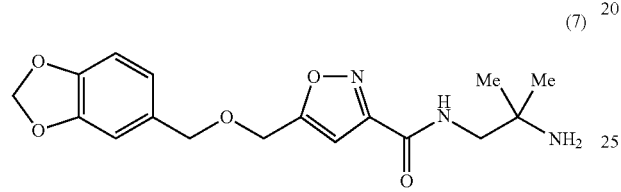

(7)

1H-NMR (DMSO-$d_6$, TMS, δ (ppm)): 8.44 (1H, s), 6.83-6.91 (4H, m), 6.60 (2H, s), 4.65 (2H, s), 4.46 (2H, s), 3.14 (2H, s), 1.64 (2H, s), 0.99 (6H, s).

Preparation Example 10

Present compounds that were prepared according to the similar method to those described in Preparation Example 9, and the physical property values were shown below.

Compounds Represented by Formula (I-1):

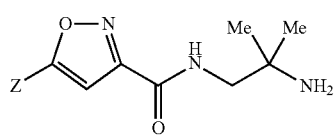

(I-1)

wherein Z represents any group indicated in [Table 1].

TABLE 1

| Present compound | Z |
|---|---|
| (8) | 5,6,7,8-tetrahydronaphthalen-2-ylmethoxymethyl group |
| (9) | 3-fluoro-4-bromobenzyloxymethyl group |
| (10) | 4-trifluoromethoxybenzyloxymethyl group |

TABLE 1-continued

| Present compound | Z |
|---|---|
| (11) | 3-methylbenzyloxymethyl group |
| (12) | 4-methoxybenzyloxymethyl group |
| (19) | benzyl-CH2- |
| (20) | 3-fluorobenzyl-CH2- |
| (23) | phenoxyethyl |
| (24) | 3-bromo-5-fluorobenzyloxymethyl |
| (25) | pyridin-2-yloxymethyl |
| (29) | F3C-CH2-CH2- |
| (30) | Me-(CH2)6- |
| (31) | cyclopentylmethyl-CH2- |
| (32) | cyclopropylmethyl |

Present Compound (8)
  1H-NMR (DMSO-$d_6$, TMS, δ (ppm)): 8.45 (1H, brs), 7.02 (3H, d), 6.82 (1H, s), 4.66 (2H, s), 4.47 (2H, s), 3.15 (2H, brs), 2.70 (4H, brs), 1.65-1.85 (6H, m), 1.00 (6H, s).

Present Compound (9)
  1H-NMR (DMSO-$d_6$, TMS, δ (ppm)): 8.67 (1H, brs), 7.70 (1H, d), 7.35 (1H, d), 7.16 (1H, d), 6.89 (1H, s), 4.74 (2H, s), 4.58 (2H, s), 3.40 (2H, brs), 3.23 (2H, s), 1.08 (6H, s).

Present Compound (10)
  1H-NMR (DMSO-$d_6$, TMS, δ (ppm)): 8.44 (1H, brs), 7.46 (2H, d), 7.35 (2H, d), 6.86 (1H, s), 4.73 (2H, s), 4.61 (2H, s), 3.14 (2H, s), 1.55 (2H, brs), 0.99 (6H, s).

Present Compound (11)
  1H-NMR (DMSO-$d_6$, TMS, δ (ppm)): 8.49 (1H, brs), 7.30-7.08 (4H, m), 6.84 (1H, s), 4.69 (2H, s), 4.53 (2H, s), 3.17 (2H, s), 2.37 (2H, brs), 2.30 (3H, s), 1.01 (6H, s).

Present Compound (12)
 ¹H-NMR (DMSO-d₅, TMS, δ (ppm)): 8.44 (1H, brs), 7.30-7.20 (2H, m), 6.95-6.88 (2H, m), 6.82 (1H, s), 4.66 (2H, s), 4.49 (2H, s), 3.74 (3H, s), 3.14 (2H, s), 1.56 (2H, brs), 0.99 (6H, s).
Present Compound (19)
 ¹H-NMR (DMSO-d₆, TMS, δ (ppm)): 8.35 (1H, brs), 7.40-7.25 (5H, m), 6.54 (1H, s), 4.20 (2H, s), 3.11 (2H, s), 1.51 (2H, brs), 0.97 (6H, s).
Present Compound (20)
 ¹H-NMR (DMSO-d₆, TMS, δ (ppm)): 8.37 (1H, brs), 7.44-7.36 (1H, m), 7.22-7.08 (3H, m), 6.58 (1H, s), 4.24 (2H, s), 3.12 (2H, s), 1.48 (2H, brs), 0.97 (6H, s).
Present Compound (23)
 1H-NMR (DMSO-do TMS, δ (ppm)): 8.51 (1H, brs), 7.36-7.28 (2H, m), 7.08-6.96 (3H, m), 6.93 (1H, s), 5.34 (2H, s), 3.15 (2H, s), 1.00 (6H, s).
Present Compound (24)
 ¹H-NMR (DMSO-d₆, TMS, δ (ppm)): 8.48 (1H, brs), 7.22-7.16 (2H, m), 7.10-7.03 (1H, m), 6.96 (1H, s), 5.41 (2H, s), 3.14 (2H, s), 1.49 (2H, brs), 0.99 (6H, s).
Present Compound (25)
 ¹H-NMR (DMSO-d6, TMS, δ (ppm)): 8.44 (1H, brs), 7.85-7.80 (1H, m), 7.52-7.44 (1H, m), 6.65 (1H, s), 6.47-6.40 (1H, m), 6.32-6.28 (1H, m), 5.32 (2H, s), 3.12 (2H, s), 1.55 (2H, brs), 0.97 (6H, s).
Present Compound (29)
 ¹H-NMR (DMSO-d₆, TMS, δ (ppm)): 8.37 (1H, brs), 6.72 (1H, s), 3.16-3.06 (4H, m), 2.84-2.68 (2H, m), 1.49 (2H, brs), 0.98 (6H, s).
Present Compound (30)
 ¹H-NMR (DMSO-do TMS, δ (ppm)): 8.32 (1H, brs), 6.56 (1H, s), 3.15-3.10 (2H, m), 2.75-2.84 (2H, m), 1.70-1.58 (2H, m), 1.58 (2H, brs), 1.34-1.16 (10H, m), 0.98 (6H, s), 0.88-0.80 (3H, m).
Present Compound (31)
 ¹H-NMR (DMSO-do TMS, δ (ppm)): 8.32 (1H, brs), 6.57 (1H, s), 3.16-3.10 (2H, m), 2.84-2.78 (2H, m), 1.80-1.40 (11H, m), 1.15-1.05 (2H, m), 0.98 (6H, s).
Present Compound (32)
 ¹H-NMR (DMSO-do TMS, δ (ppm)): 8.34 (1H, brs), 6.61 (1H, s), 3.16-3.10 (2H, m), 2.72 (2H, d), 1.48 (2H, brs), 1.02-1.10 (1H, m), 0.99 (6H, s), 0.60-0.50 (2H, m), 0.28-0.20 (2H, m).

Preparation Example 11

Intermediate compound (3A) that is described in Reference Preparation Example 2 (0.62 g, 1.35 mmol) was dissolved in 1,4-dioxane (2 mL), and thereto was added slowly 4 mol/L hydrogen chloride (1,4-dioxane solution, 10 mL) under ice-cooling. The mixture was stirred at room temperature for 3 hours, and concentrated under reduced pressure. To the resulting residues were added ethanol and amberlyst A21, and the mixtures were stirred at room temperature for 5 hours. The reaction solutions were filtered, and the filtrates were concentrated under reduced pressure to give 0.34 g of Present compound (13) represented by the following formula.

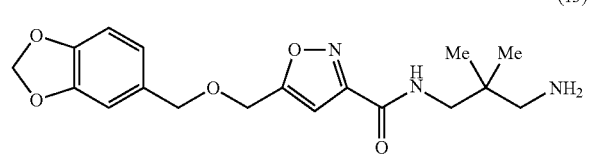

(13)

¹H-NMR (DMSO-d₆, TMS, δ (ppm)): 8.91 (1H, s), 6.95-6.78 (4H, m), 6.00 (2H, s), 4.65 (2H, s), 4.46 (2H, s), 3.12 (2H, s), 2.34 (2H, s), 0.81 (6H, s).

Preparation Example 12

The compounds that were prepared by using each Intermediate compound that is described in Reference Preparation Example 3, and physical property values thereof are shown below.

Compounds Represented by Formula (I-2):

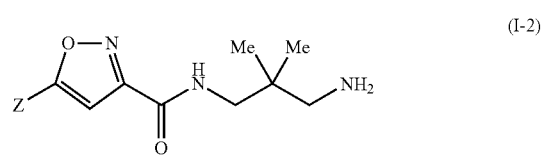

(I-2)

wherein Z represents any group indicated in [Table 2]

TABLE 2

| Present compound | Z |
|---|---|
| (14) | ![tetrahydronaphthalenyl-CH2-O-CH2-] |
| (15) | ![4-Br-3-F-phenyl-CH2-O-CH2-] |
| (16) | ![4-F3CO-phenyl-CH2-O-CH2-] |
| (17) | ![3-Me-phenyl-CH2-O-CH2-] |
| (18) | ![4-MeO-phenyl-CH2-O-CH2-] |
| (21) | ![phenyl-CH2-] |
| (22) | ![3-F-phenyl-CH2-] |
| (26) | ![phenyl-O-CH2-] |

TABLE 2-continued

| Present compound | Z |
|---|---|
| (27) | 3-bromo-5-fluorophenoxyethyl group |
| (28) | pyridin-2-yloxyethyl group |
| (33) | 3,3,3-trifluoropropyl group |
| (34) | n-nonyl group (Me-(CH2)8-) |
| (35) | 2-cyclopentylethyl group |
| (36) | cyclopropylmethyl group |

Present compound (14)

$^1$H-NMR (DMSO-$d_6$, TMS, δ (ppm)): 8.92 (1H, brs), 7.05-6.99 (3H, m), 6.80 (1H, s), 4.66 (2H, s), 4.47 (2H, s), 3.16 (2H, s), 2.69 (4H, brs), 2.34 (2H, s), 1.72 (4H, brs), 0.81 (6H, s).

Present Compound (15)

$^1$H-NMR (DMSO-$d_6$, TMS, δ (ppm)): 8.93 (1H, brs), 7.69 (1H, dd), 7.35 (1H, d), 7.15 (1H, d), 6.85 (1H, s), 4.73 (2H, s), 4.58 (2H, s), 3.13 (2H, s), 2.39 (2H, s), 0.83 (6H, s).

Present Compound (16)

$^1$H-NMR (DMSO-$d_6$, TMS, δ (ppm)): 8.95 (1H, brs), 7.48 (2H, d), 7.35 (2H, d), 6.86 (1H, s), 4.69 (2H, s), 4.61 (2H, s), 3.15 (2H, s), 2.46 (2H, s), 0.86 (6H, s).

Present Compound (16)

$^1$H-NMR (DMSO-$d_6$, TMS, δ (ppm)): 8.92 (1H, brs), 7.29-7.08 (4H, m), 6.82 (1H, s), 4.65 (2H, s), 4.53 (2H, s), 3.06 (2H, s), 2.38 (2H, s), 2.30 (3H, s), 0.82 (6H, s).

Present Compound (18)

$^1$H-NMR (DMSO-$d_6$, TMS, δ (ppm)): 8.93 (1H, brs), 7.30-7.24 (2H, m), 6.95-6.88 (2H, m), 6.63 (1H, s), 4.65 (2H, s), 4.48 (2H, s), 3.74 (3H, s), 3.12 (2H, s), 2.34 (2H, s), 0.81 (6H, s).

Present Compound (21)

$^1$H-NMR (DMSO-$d_6$, TMS, δ (ppm)): 8.90 (1H, brs), 7.40-7.25 (5H, m), 6.56 (1H, s), 4.21 (2H, s), 3.20-3.13 (2H, m), 2.57 (2H, s), 0.90 (6H, s).

Present Compound (22)

$^1$H-NMR (DMSO-$d_6$, TMS, δ (ppm)): 8.91 (1H, brs), 7.78-7.10 (6H, m), 6.60 (1H, s), 4.25 (2H, s), 3.16 (2H, s), 2.60 (2H, s), 0.91 (6H, s).

Present Compound (26)

$^1$H-NMR (DMSO-$d_6$, TMS, δ (ppm)): 9.00 (1H, brs), 7.38-7.18 (2H, m), 7.08-6.97 (3H, m), 6.94 (1H, s), 5.34 (2H, s), 3.16 (2H, s), 2.52 (2H, s), 0.88 (6H, s).

Present Compound (27)

$^1$H-NMR (DMSO-$d_6$, TMS, δ (ppm)): 8.99 (1H, brs), 7.22-7.16 (2H, m), 7.10-7.04 (1H, m), 6.95 (1H, s), 5.41 (2H, s), 3.14 (2H, s), 2.44 (2H, s), 0.85 (6H, s).

Present Compound (28)

$^1$H-NMR (DMSO-$d_6$, TMS, δ (ppm)): 9.00 (1H, brs), 8.22-8.15 (1H, m), 7.92-7.73 (3H, m), 7.10-7.04 (1H, m), 6.97-6.86 (2H, m), 5.55 (2H, s), 3.25-3.15 (2H, s), 2.63 (2H, s), 0.93 (6H, s).

Present Compound (33)

$^1$H-NMR (DMSO-$d_6$, TMS, δ (ppm)): 8.94 (1H, brs), 6.80 (2H, brs), 6.74 (1H, s), 3.20-3.05 (4H, m), 2.82-2.65 (2H, m), 2.56 (2H, s), 0.90 (6H, s).

Present Compound (34)

$^1$H-NMR (DMSO-$d_6$, TMS, δ (ppm)): 8.87 (1H, brs), 7.40 (2H, brs), 6.55 (1H, s), 3.16-3.11 (2H, m), 2.80-2.72 (2H, m), 2.56 (2H, s), 1.67-1.56 (2H, m), 1.30-1.18 (10H, m), 0.88 (6H, s), 0.85-0.80 (3H, m).

Present Compound (35)

$^1$H-NMR (DMSO-$d_6$, TMS, δ (ppm)): 8.89 (1H, brs), 6.99 (2H, brs), 6.59 (1H, s), 3.20-3.12 (2H, m), 2.84-2.76 (2H, m), 2.56 (2H, s), 1.80-1.42 (9H, m), 1.16-1.02 (2H, m), 0.90 (6H, s).

Present Compound (36)

$^1$H-NMR (DMSO-$d_6$, TMS, δ (ppm)): 8.84 (1H, brs), 6.58 (1H, s), 3.11 (2H, s), 2.71 (2H, d), 2.33 (2H, s), 1.71 (2H, brs), 1.10-1.00 (1H, m), 0.80 (6H, s), 0.57-0.48 (2H, m), 0.29-0.19 (2H, m).

Reference Preparation Example 1

Intermediate compound (1A) (0.50 g, 2.96 mmol) was dissolved into ethyl acetate (15 mL), and thereto was added DMF (0.01 mL). To the mixture solution was added thionyl chloride (0.26 mL, 3.55 mmol), and the mixture was stirred at 80° C. for 1 hour. The reaction mixture was then cooled to room temperature, and concentrated under reduced pressure. To the resulting concentrates was added toluene (0.5 mL). The solutions were added to a mixed solution of N-(tert-butoxycarbonyl)-2,2-dimethylpropane-1,3-diamine (0.60 g, 1.42 mmol) and 1N aqueous sodium hydroxide solution (7.4 mL) under ice-cooling. The mixture was stirred at the same temperature for 1 hour, and the reaction mixture was then extracted with ethyl acetate twice. The organic layers were washed with saturated brine, dried over anhydrous magnesium sulfate, and concentrated under reduced pressure. The residues were subjected to silica gel column chromatography to give 1.04 g of a compound represented by formula (6) (hereinafter, referred to as Compound (6)) and Intermediate compound (2A) represented by the following formula.

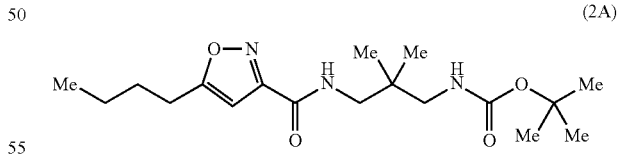

(2A)

$^1$H-NMR (CDCl$_3$, TMS, δ (ppm)): 7.59-7.55 (1H, m), 6.43 (1H, s), 5.30-5.25 (1H, m), 3.21 (2H, d), 2.93 (2H, d), 2.79 (2H, t), 1.73-1.66 (2H, m), 1.45 (9H, s), 1.40 (2H, dd), 0.94 (3H, t), 0.92 (6H, s).

Reference Preparation Example 2

The compound represented by the following formula (3A) (hereinafter, referred to as Intermediate compound (3A)) was prepared by using (3-amino-2,2-dimethylpropyl)carbamic acid tert-butyl ester in the place of 2-methylpropane- 1,2-diamine according to the similar method to those described in Preparation Example 9.

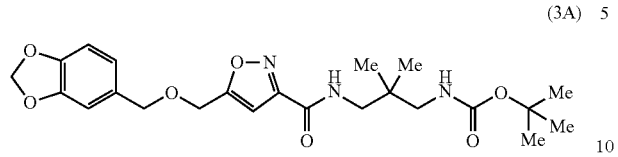
(3A)

$^1$H-NMR (DMSO-$d_6$, TMS, δ (ppm)): 8.62 (1H, s), 6.92-6.81 (5H, m), 6.00 (2H, s), 4.66 (2H, s), 4.46 (2H, s), 3.05 (2H, d), 2.77 (2H, d), 1.38 (9H, s), 0.78 (6H, s).

Reference Preparation Example 3

The compounds that were prepared according to the similar method to those described in Reference Preparation Example 2, and physical property values thereof are shown below.

The compounds represented by formula (M):

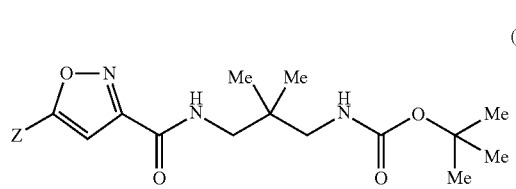
(M)

wherein Z represents any group indicated in [Table 3].

TABLE 3

| Intermediate compound | Z |
|---|---|
| (4A) | tetrahydronaphthalenyl-CH₂-O-CH₂-CH₂-• |
| (5A) | 4-Br-3-F-C₆H₃-CH₂-O-CH₂-CH₂-• |
| (6A) | 4-F₃CO-C₆H₄-CH₂-O-CH₂-CH₂-• |
| (7A) | 3-Me-C₆H₄-CH₂-O-CH₂-CH₂-• |
| (8A) | 4-MeO-C₆H₄-CH₂-O-CH₂-CH₂-• |
| (9A) | C₆H₅-CH₂-• |

TABLE 3-continued

| Intermediate compound | Z |
|---|---|
| (10A) | 3-F-C₆H₄-CH₂-• |
| (11A) | C₆H₅-O-CH₂-CH₂-• |
| (12A) | 3-Br-5-F-C₆H₃-O-CH₂-CH₂-• |
| (13A) | 2-pyridyl-O-CH₂-CH₂-• |
| (14A) | F₃C-CH₂-CH₂-• |
| (15A) | Me-(CH₂)₆-CH₂-• |
| (16A) | cyclopentyl-CH₂-CH₂-• |
| (17A) | cyclopropyl-CH₂-• |

Intermediate Compound (4A)
$^1$H-NMR (DMSO-$d_6$, TMS, δ (ppm)): 8.66-8.60 (1H, m), 7.05-7.00 (3H, m), 6.92-6.87 (1H, m), 6.80 (1H, s), 4.66 (2H, s), 4.47 (2H, s), 3.10-3.00 (2H, m), 2.80-2.75 (2H, m), 2.69 (4H, brs), 1.71 (4H, brs), 1.38 (9H, s), 0.78 (6H, s).

Intermediate Compound (5A)
$^1$H-NMR (DMSO-$d_6$, TMS, δ (ppm)): 8.62 (1H, brs), 7.74-7.66 (1H, m), 7.39-7.31 (1H, m), 7.20-7.12 (1H, m), 6.92-6.82 (2H, m), 4.74 (2H, s), 4.58 (2H, s), 3.09-3.01 (2H, m), 2.81-2.73 (2H, m), 1.38 (9H, s), 0.78 (6H, s).

Intermediate Compound (6A)
$^1$H-NMR (DMSO-$d_6$, TMS, δ (ppm)): 8.65-8.61 (1H, m), 7.48 (2H, d), 7.35 (2H, d), 6.92-6.87 (1H, m), 6.84 (1H, s), 4.74 (2H, s), 4.61 (2H, s), 3.08-3.01 (2H, m), 2.80-2.74 (2H, m), 1.38 (9H, s), 0.78 (6H, s).

Intermediate Compound (7A)
$^1$H-NMR (DMSO-$d_6$, TMS, δ (ppm)): 8.68-8.60 (1H, m), 7.27-7.09 (4H, m), 6.92-6.85 (1H, m), 6.82 (1H, s), 4.69 (2H, s), 4.53 (2H, s), 3.10-3.01 (2H, m), 2.81-2.73 (2H, m), 2.30 (3H, s), 1.38 (9H, s), 0.78 (6H, s).

Intermediate Compound (8A)
$^1$H-NMR (DMSO-$d_6$, TMS, δ (ppm)): 8.68-8.54 (1H, m), 7.31-7.24 (2H, m), 6.95-6.82 (3H, m), 6.80 (1H, s), 4.66 (2H, s), 4.49 (2H, s), 3.74 (3H, s), 3.08-3.01 (2H, m), 2.80-2.73 (2H, m), 1.38 (9H, s), 0.78 (6H, s).

Intermediate Compound (9A)
$^1$H-NMR (DMSO-$d_6$, TMS, δ (ppm)): 8.58-8.51 (1H, m), 7.39-7.24 (5H, m), 6.70-6.82 (1H, m), 6.52 (1H, s), 4.20 (2H, s), 3.05-2.99 (2H, m), 2.79-2.71 (2H, m), 1.37 (9H, s), 0.77 (6H, s).

Intermediate Compound (10A)

¹H-NMR (DMSO-d₆, TMS, δ (ppm)): 8.59-8.52 (1H, m), 7.44-7.39 (1H, m), 7.21-7.08 (3H, m), 6.90-6.83 (1H, m), 6.56 (1H, s), 4.24 (2H, s), 3.05-2.99 (2H, m), 2.79-2.72 (2H, m), 1.37 (9H, s), 0.77 (6H, s).

Intermediate Compound (11A)

¹H-NMR (DMSO-d₆, TMS, δ (ppm)): 8.68-8.61 (1H, m), 7.36-7.28 (2H, m), 7.09-6.84 (5H, m), 5.34 (2H, s), 3.08-3.02 (2H, m), 2.80-2.74 (2H, m), 1.38 (9H, s), 0.78 (6H, s).

Intermediate Compound (12A)

¹H-NMR (DMSO-d₆, TMS, δ (ppm)): 8.69-8.64 (1H, m), 7.22-7.15 (2H, m), 7.10-7.03 (1H, m), 6.95 (1H, s), 6.91-6.87 (1H, m), 5.41 (2H, s), 3.07-3.02 (2H, m), 2.80-2.74 (2H, m), 1.38 (9H, s), 0.78 (6H, s).

Intermediate Compound (13A)

¹H-NMR (DMSO-d₆, TMS, δ (ppm)): 8.68-8.60 (1H, m), 8.22-8.17 (1H, m), 8.22-8.17 (1H, m), 7.81-7.72 (1H, m), 7.09-7.03 (1H, m), 6.95-6.85 (1H, m), 6.84 (1H, s), 5.44 (2H, s), 3.06-3.01 (2H, m), 2.79-2.74 (2H, m), 1.38 (9H, s), 0.77 (6H, s).

Intermediate Compound (14A)

¹H-NMR (DMSO-do TMS, δ (ppm)): 8.61-8.54 (1H, m), 6.93-6.86 (1H, m), 6.71 (1H, s), 3.13-3.01 (4H, m), 2.85-2.70 (4H, m), 1.38 (9H, s), 0.78 (6H, s).

Intermediate Compound (15A)

¹H-NMR (DMSO-do TMS, δ (ppm)): 8.57-8.50 (1H, m), 6.91-6.88 (1H, m), 6.55 (1H, s), 3.06-3.00 (2H, m), 2.83-2.74 (4H, m), 1.66-1.60 (2H, m), 1.38 (9H, s), 1.33-1.21 (10H, m), 0.87-0.81 (3H, m), 0.78 (6H, s).

Intermediate Compound (16A)

¹H-NMR (DMSO-d6, TMS, δ (ppm)): 8.56-8.49 (1H, m), 6.91-6.86 (1H, m), 6.56 (1H, s), 3.05-3.01 (2H, m), 2.84-2.73 (4H, m), 1.78-1.42 (9H, m), 1.38 (9H, s), 1.17-1.04 (2H, m), 0.77 (6H, s).

Intermediate Compound (17A)

¹H-NMR (DMSO-do TMS, δ (ppm)): 8.55 (1H, brs), 6.89 (1H, brs), 6.60 (1H, s), 3.05-3.02 (2H, m), 2.79-2.70 (4H, m), 1.38 (9H), 1.09-1.02 (1H, m), 0.78 (6H, s), 0.56-0.51 (2H, m), 0.25-0.21 (2H, m).

Reference Preparation Example 4

To a solution of Intermediate compound (22A) that was described in Reference Preparation Example 6 (5 g, 21.1 mmol) in THF (20 mL) was added 5 N aqueous sodium hydroxide solution (4 mL) while the temperature of the reaction system was being kept at 0 to 10° C. in an ice bath, and the mixture was stirred at room temperature for 5 hours. To the reaction solution was then added dropwise slowly 6 N aqueous hydrochloric acid solution such that the pH of the reaction solution was adjusted to pH 2 to 3. The mixture was allowed to stand for 5 minutes, and the precipitated materials were filtered off, and the residues were washed successively with water and pentane. The resulting solids were dried under reduced pressure to give 4.1 g of a compound represented by the following formula (18A) (hereinafter, referred to as Intermediate compound (18A)).

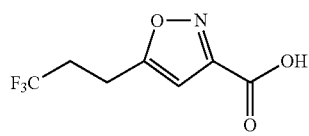
(18A)

¹H-NMR (DMSO-d₆, TMS, δ (ppm)): 14.01 (1H, brs), 6.75 (1H, s), 3.13-3.05 (2H, m), 2.84-2.69 (2H, m).

Reference Preparation Example 5

The compounds that were prepared by using each Intermediate compound that is described in Reference Example 7 according to the similar method to those described in Reference Preparation Example 4, and physical property values are shown below.

The compounds represented by formula (N):

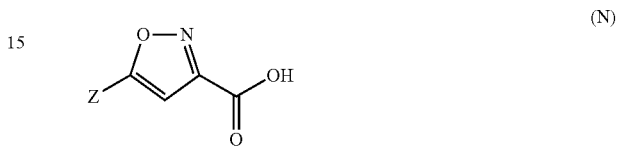

wherein Z represents any group indicated in [Table 4].

TABLE 4

| Intermediate compound | Z |
|---|---|
| (19A) | Me~~~~~• |
| (20A) | cyclopentyl-CH₂CH₂-• |
| (21A) | cyclopropyl-CH₂-• |
| (31A) | 2-pyridyl-O-CH₂-• |

Intermediate Compound (19A)

¹H-NMR (DMSO-d₆, TMS, δ (ppm)): 14.03 (1H, brs), 6.55 (1H, s), 2.83-2.75 (2H, m), 1.70-1.58 (2H, m), 1.34-1.18 (10H, m), 0.90-0.82 (3H, m).

Intermediate Compound (20A)

¹H-NMR (DMSO-d₆, TMS, δ (ppm)): 13.87 (1H, brs), 6.59 (1H, s), 2.84-2.76 (2H, m), 1.79-1.41 (9H, m), 1.18-1.02 (2H, m).

Intermediate Compound (21A)

¹H-NMR (DMSO-d₆, TMS, δ (ppm)): 13.78 (1H, brs), 6.62 (1H, s), 2.75-2.69 (2H, m), 1.10-1.01 (1H, m), 0.55-0.50 (2H, m), 0.26-0.21 (2H, Intermediate Compound (31A)

¹H-NMR (DMSO-d₆, TMS, δ (ppm)): 14.04 (1H, brs), 7.85-7.80 (1H, m), 7.51-7.44 (1H, m), 6.67 (1H, s), 6.46-6.40 (1H, m), 6.32-6.27 (1H, m), 5.32 (2H, m).

Reference Preparation Example 6

To a solution of Intermediate compound (26A) that is described in Reference Preparation Example 8 (5 g, 20.8 mmol) in ethanol (50 mL) was added hydroxylamine hydrochloride (2.9 g, 41.6 mmol), and the mixture was stirred for 16 hours at reflux under nitrogen atmosphere. The temperature of the reaction solutions was returned to room temperature, and the mixture was concentrated under reduced pressure. To the resulting residues was added water, and the mixture was extracted with ethyl acetate twice. The organic layers were washed with saturated brine, dried over anhydrous sodium sulfate, and concentrated under reduced pressure. The residues were subjected to silica gel column chromatography to give 4.6 g of Intermediate compound (22A) represented by the following formula.

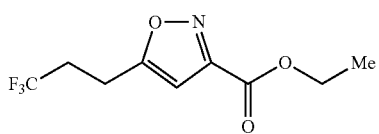

(22A)

$^1$H-NMR (CDCl$_3$, TMS, δ (ppm)): 6.49 (1H, s), 4.42 (2H, q), 3.13-3.06 (2H, m), 2.62-2.46 (2H, m), 1.40 (3H, t).

Reference Preparation Example 7

The compounds that were prepared by using each Intermediate compound that is described in Reference Example 9 according to the similar method to those described in Reference Preparation Example 6, and physical property values thereof are shown below.

The compounds represented by formula (O):

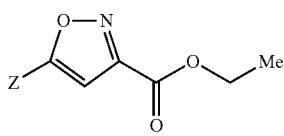

(O)

wherein Z represents any group indicated in [Table 5].

TABLE 5

| Intermediate compound | Z |
|---|---|
| (23A) | Me~~~~• |
| (24A) | (cyclopentyl-CH$_2$CH$_2$-) |
| (25A) | (cyclopropyl-CH$_2$-) |

Intermediate Compound (23A)

$^1$H-NMR (CDCl$_3$, TMS, δ (ppm)): 6.38 (1H, s), 4.40 (2H, q), 2.81-2.67 (2H, m), 1.73-1.65 (2H, m), 1.43-1.18 (13H, m), 0.89-0.82 (3H, m).

Intermediate Compound (24A)

$^1$H-NMR (CDCl$_3$, TMS, δ (ppm)): 6.37 (1H, s), 4.38 (2H, q), 2.82-2.67 (2H, m), 1.82-1.42 (9H, m), 1.38 (3H, t), 1.18-1.02 (2H, m).

Intermediate Compound (25A)

$^1$H-NMR (CDCl$_3$, TMS, δ (ppm)): 6.50 (1H, s), 4.42 (2H, q), 2.69 (2H, d), 1.40 (3H, t), 1.08-1.01 (1H, m), 0.64-0.56 (2H, m), 0.26-0.21 (2H, m).

Reference Preparation Example 8

To a solution of diethyl oxalate (5 g, 35.7 mmol) and 5,5,5-trifuoropentan-2-one in THF (30 mL) were added slowly potassium tert-butoxide (5 g, 46.4 mmol) and THF (10 mL) under nitrogen atmosphere while the temperature of the reaction system was being kept to −20 to −15° C. in an ice/sodium chloride bath. The reaction mixture was stirred at −30 to −20° C. for 30 minutes, and raised to room temperature, and stirred for additional 16 hours. Thereto was added slowly 1N hydrochloric acid while the reaction mixture was being cooled such that the pH of the mixture was adjusted to pH 2 to 3. The mixture was extracted with ethyl acetate twice. The organic layers were washed with saturated brine, dried over anhydrous sodium sulfate, and concentrated under reduced pressure. The residues were subjected to silica gel column chromatography to give 5 g of Intermediate compound (26A) represented by the following formula.

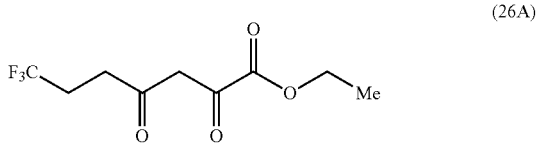 [SMILES: CCOC(=O)C(=O)CC(=O)CCC(F)(F)F]

(26A)

$^1$H-NMR (CDCl$_3$, TMS, δ (ppm)): 13.96 (1H, brs), 6.39 (1H, s), 4.35 (2H, q), 2.83-2.76 (2H, m), 2.57-2.41 (2H, m), 1.36 (3H, t).

Reference Preparation Example 9

The compounds that were prepared according to the similar method to those described in Reference Preparation Example 8, and physical property values are shown below.

The compounds represented by formula (P):

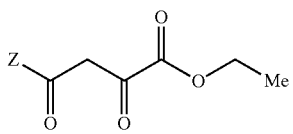

(P)

wherein Z represents any group indicated in [Table 6].

TABLE 6

| Intermediate compound | Z |
|---|---|
| (27A) | Me~~~~• |
| (28A) | (cyclopentyl-CH$_2$CH$_2$-) |
| (29A) | (cyclopropyl-CH$_2$-) |

Intermediate Compound (27A)

$^1$H-NMR (CDCl$_3$, TMS, δ (ppm)): 14.50 (1H, brs), 6.34 (1H, s), 4.39-4.30 (2H, m), 2.50-2.45 (2H, m), 1.67-1.59 (2H, m), 1.40-1.20 (13H, m), 0.88-0.83 (3H, m).

Intermediate Compound (28A)

$^1$H-NMR (CDCl$_3$, TMS, δ (ppm)): 14.49 (1H, brs), 6.35 (1H, s), 4.39-4.29 (2H, m), 2.52-2.45 (2H, m), 1.82-1.45 (9H, m), 1.36 (3H, t), 1.17-1.02 (2H, m).

Intermediate Compound (29A)

$^1$H-NMR (CDCl$_3$, TMS, δ (ppm)): 14.51 (1H, brs), 6.43 (1H, s), 4.39-4.30 (2H, m), 2.42-2.33 (2H, m), 1.36 (3H, t), 1.08-0.94 (1H, m), 0.62-0.55 (2H, m), 0.20-0.12 (2H, m).

Reference Preparation Example 10

To a solution of ethyl 5-bromomethyl-3-isoxazole carboxylate (5 g, 21.3 mmol) in DMF (30 mL) were added successively pyridin-2-ol (2.4 g, 25.6 mmol) and potassium carbonate (7 g, 51.2 mmol) at room temperature, and the mixture was stirred at 70° C. for 16 hours. The temperature of the reaction solution was returned to room temperature, and thereto was then added water, and the mixture was extracted with ethyl acetate twice. The organic layers were washed with saturated brine, dried over anhydrous sodium sulfate, and concentrated under reduced pressure. The residues were subjected to silica gel column chromatography to 2 g of Intermediate compound (30A) represented by the following formula.

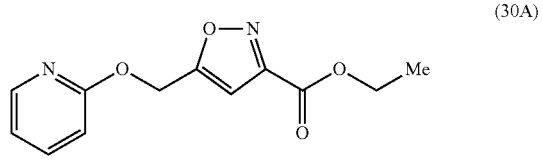 [SMILES: CCOC(=O)c1cc(COc2ccccn2)on1]
(30A)

Intermediate Compound (30A)

$^1$H-NMR (DMSO-d6, TMS, δ (ppm)): 7.86-7.80 (1H, m), 7.51-7.43 (1H, m), 6.74 (1H, s), 6.43 (1H, d), 6.34-6.26 (1H, m), 5.33 (2H, m), 4.34 (2H, q), 1.28 (3H, t).

The amide compounds represented by formula (Y-1) to formula (Y-47) can be obtained according to the similar method to the above-mentioned method. In the below-mentioned [U$^1$] and [U$^2$], Ph represents phenyl, NA1 represents naphthalen-1-yl, NA2 represents naphthalen-2-yl, IN1 represents indan-1-yl, IN2 represents indan-2-yl, Py2 represents 2-pyridyl, Qun2 represents 2-quinolyl, Fur2 represents 2-furyl, Thi2 represents 2-thienyl, BF5 represents 5-benzofuranyl, BF2 represents 2-benzofuranyl, BT5 represents 5-benzothienyl, BT2 represents 2-benzothienyl, BDXO5 represents 1,3-benzodioxol-5-yl, BDXA6 represents 1,4-benzodioxan-6-yl, 3Cy represents cyclopropyl, 5Cy represents cyclopentyl, 8Cy represents cyclooctyl, and TN represents tetrahydronaphthalen-2-yl.

For example, [CH$_2$CH$_2$CH$_2$Ph] represents 3-phenylpropyl, [CH$_2$CH$_2$(8-F-NA2)] represents 2-(8-fluoronaphthalen-2-yl)ethyl, and [CH$_2$CH$_2$(2,2-F$_2$-3Cy)] represents 2-(2,2-difluorocyclopropyl)ethyl.

The compounds represented by formula (Y-1) to formula (Y-19) [wherein U$^1$ represents any group selected from the following Group (U-1)]

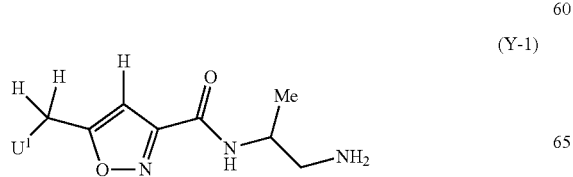
(Y-1)

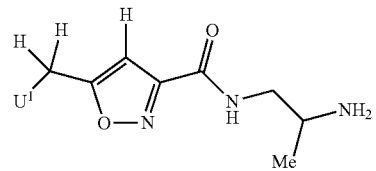
(Y-2)

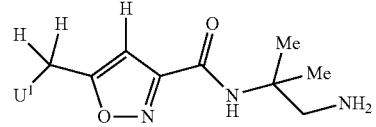
(Y-3)

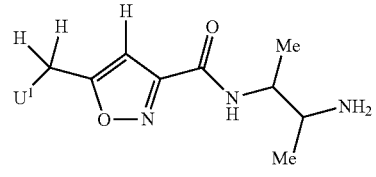
(Y-4)

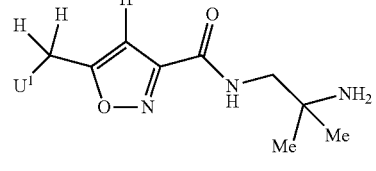
(Y-5)

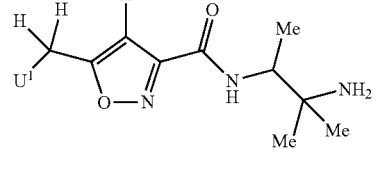
(Y-6)

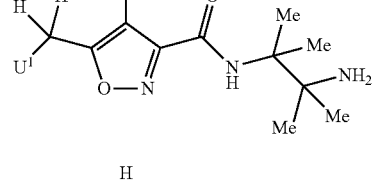
(Y-7)

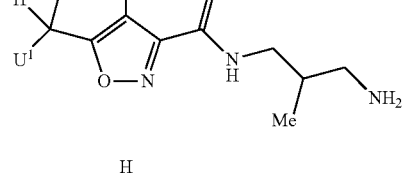
(Y-8)

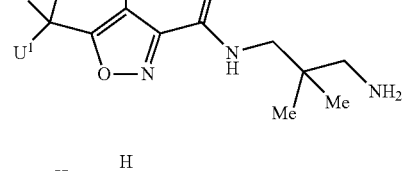
(Y-9)

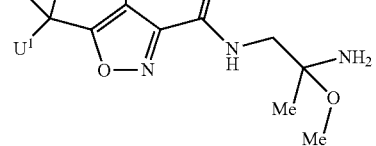
(Y-10)

(Y-11)

(Y-12)

(Y-13)

(Y-14)

(Y-15)

(Y-16)

(Y-17)

(Y-18)

(Y-19)

(Group U-1)

[U$^1$]=[H], [CH$_3$], [CH$_2$CH$_3$], [CH$_2$CH$_2$CH$_3$], [CH$_2$CH$_2$CH$_2$CH$_3$], [CH$_2$CH$_2$CH$_2$CH$_2$CH$_3$], [CH$_2$CH$_2$CH$_2$CH$_2$CH$_2$CH$_3$], [CH$_2$CH$_2$CH$_2$CH$_2$CH$_2$CH$_2$CH$_3$], [CH$_2$CF$_3$], [CH$_2$CH$_2$CF$_3$], [CH$_2$CH$_2$CH$_2$CF$_3$], [CH$_2$CH$_2$CH$_2$CH$_2$CF$_3$], [Ph], [CH$_2$Ph], [CH$_2$CH$_2$Ph], [CH$_2$CH$_2$CH$_2$Ph], [CH$_2$CH$_2$CH$_2$CH$_2$Ph], [2-F-Ph], [CH$_2$(2-F-Ph)], [CH$_2$CH$_2$(2-F-Ph)], [CH$_2$CH$_2$CH$_2$(2-F-Ph)], [CH$_2$CH$_2$CH$_2$CH$_2$(2-F-Ph)], [3-F-Ph], [CH$_2$(3-F-Ph)], [CH$_2$CH$_2$(3-F-Ph)], [CH$_2$CH$_2$CH$_2$(3-F-Ph)], [CH$_2$CH$_2$CH$_2$CH$_2$(3-F-Ph)], [4-F-Ph], [CH$_2$(4-F-Ph)], [CH$_2$CH$_2$(4-F-Ph)], [CH$_2$CH$_2$CH$_2$(4-F-Ph)], [CH$_2$CH$_2$CH$_2$CH$_2$(4-F-Ph)], [2-Cl-Ph], [CH$_2$(2-Cl-Ph)], [CH$_2$CH$_2$(2-Cl-Ph)], [CH$_2$CH$_2$CH$_2$(2-Cl-Ph)], [CH$_2$CH$_2$CH$_2$CH$_2$(2-Cl-Ph)], [3-Cl-Ph], [CH$_2$(3-Cl-Ph)], [CH$_2$CH$_2$(3-Cl-Ph)], [CH$_2$CH$_2$CH$_2$(3-Cl-Ph)], [CH$_2$CH$_2$CH$_2$CH$_2$(3-Cl-Ph)], [4-Cl-Ph], [CH$_2$(4-Cl-Ph)], [CH$_2$CH$_2$(4-Cl-Ph)], [CH$_2$CH$_2$CH$_2$(4-Cl-Ph)], [CH$_2$CH$_2$CH$_2$CH$_2$(4-Cl-Ph)], [2-Br-Ph], [CH$_2$(2-Br-Ph)], [CH$_2$CH$_2$(2-Br-Ph)], [CH$_2$CH$_2$CH$_2$(2-Br-Ph)], [CH$_2$CH$_2$CH$_2$CH$_2$(2-Br-Ph)], [3-Br-Ph], [CH$_2$(3-Br-Ph)], [CH$_2$CH$_2$(3-Br-Ph)], [CH$_2$CH$_2$CH$_2$(3-Br-Ph)], [CH$_2$CH$_2$CH$_2$CH$_2$(3-Br-Ph)], [4-Br-Ph], [CH$_2$(4-Br-Ph)], [CH$_2$CH$_2$(4-Br-Ph)], [CH$_2$CH$_2$CH$_2$(4-Br-Ph)], [CH$_2$CH$_2$CH$_2$CH$_2$(4-Br-Ph)], [3-Br-5-F-Ph], [CH$_2$(3-Br-5-F-Ph)], [CH$_2$CH$_2$(3-Br-5-F-Ph)], [CH$_2$CH$_2$CH$_2$(3-Br-5-F-Ph)], [CH$_2$CH$_2$CH$_2$CH$_2$(3-Br-5-F-Ph)], [CH$_2$(4-Br-3-F-Ph)], [CH$_2$CH$_2$(4-Br-3-F-Ph)], [CH$_2$CH$_2$CH$_2$(4-Br-3-F-Ph)], [3-Me-Ph], [CH$_2$(3-Me-Ph)], [CH$_2$CH$_2$(3-Me-Ph)], [CH$_2$CH$_2$CH$_2$(3-Me-Ph)], [2-CF$_3$-Ph], [CH$_2$(2-CF$_3$-Ph)], [CH$_2$CH$_2$(2-CF$_3$-Ph)], [CH$_2$CH$_2$CH$_2$(2-CF$_3$-Ph)], [CH$_2$CH$_2$CH$_2$CH$_2$(2-CF$_3$-Ph)], [3-CF$_3$-Ph], [CH$_2$(3-CF$_3$-Ph)], [CH$_2$CH$_2$(3-CF$_3$-Ph)], [CH$_2$CH$_2$CH$_2$(3-CF$_3$-Ph)], [CH$_2$CH$_2$CH$_2$CH$_2$(3-CF$_3$-Ph)], [4-CF$_3$-Ph], [CH$_2$(4-CF$_3$-Ph)], [CH$_2$CH$_2$(4-CF$_3$-Ph)], [CH$_2$CH$_2$CH$_2$(4-CF$_3$-Ph)], [CH$_2$CH$_2$CH$_2$CH$_2$(4-CF$_3$-Ph)], [3-OMe-Ph], [CH$_2$(3-OMe-Ph)], [CH$_2$CH$_2$(3-OMe-Ph)], [CH$_2$CH$_2$CH$_2$(3-OMe-Ph)], [4-OMe-Ph], [CH$_2$(4-OMe-Ph)], [CH$_2$CH$_2$(4-OMe-Ph)], [CH$_2$CH$_2$CH$_2$(4-OMe-Ph)], [2-OCF$_3$-Ph], [CH$_2$(2-OCF$_3$-Ph)], [CH$_2$CH$_2$(2-OCF$_3$-Ph)], [CH$_2$CH$_2$CH$_2$(2-OCF$_3$-Ph)], [CH$_2$CH$_2$CH$_2$CH$_2$(2-OCF-Ph)], [3-OCF$_3$-Ph], [CH$_2$(3-OCF$_3$-Ph)], [CH$_2$CH$_2$(3-OCF$_3$-Ph)], [CH$_2$CH$_2$CH$_2$(3-OCF$_3$-Ph)], [CH$_2$CH$_2$CH$_2$CH$_2$(3-OCF$_3$-Ph)], [4-OCF$_3$-Ph], [CH$_2$(4-OCF$_3$-Ph)], [CH$_2$CH$_2$(4-OCF$_3$-Ph)], [CH$_2$CH$_2$CH$_2$(4-OCF$_3$-Ph)], [CH$_2$CH$_2$CH$_2$CH$_2$(4-OCF$_3$-Ph)], [2-SCF$_3$-Ph], [CH$_2$(2-SCF$_3$-Ph)], [CH$_2$CH$_2$(2-SCF$_3$-Ph)], [CH$_2$CH$_2$CH$_2$(2-SCF$_3$-Ph)], [CH$_2$CH$_2$CH$_2$CH$_2$(2-SCF$_3$-Ph)], [3-SCF$_3$-Ph], [CH$_2$(3-SCF$_3$-Ph)], [CH$_2$CH$_2$(3-SCF$_3$-Ph)], [CH$_2$CH$_2$CH$_2$(3-SCF$_3$-Ph)], [CH$_2$CH$_2$CH$_2$CH$_2$(3-SCF$_3$-Ph)], [4-SCF$_3$-Ph], [CH$_2$(4-SCF$_3$-Ph)], [CH$_2$CH$_2$(4-SCF$_3$-Ph)], [CH$_2$CH$_2$CH$_2$(4-SCF$_3$-Ph)], [CH$_2$CH$_2$CH$_2$CH$_2$(4-SCF$_3$-Ph)], [NA1], [CH$_2$(NA1)], [CH$_2$CH$_2$(NA1)], [CH$_2$CH$_2$CH$_2$(NA1)], [CH$_2$CH$_2$CH$_2$CH$_2$(NA1)], [NA2], [CH$_2$(NA2)], [CH$_2$CH$_2$(NA2)], [CH$_2$CH$_2$CH$_2$(NA2)], [8-F-NA2], [CH$_2$(8-F-NA2)], [CH$_2$CH$_2$(8-F-NA2)], [CH$_2$CH$_2$CH$_2$(8-F-NA2)], [8-Cl-NA2], [CH$_2$(8-Cl-NA2)],

[CH₂CH₂(8-Cl-NA2)], [CH₂CH₂CH₂(8-Cl-NA2)], [8-Br-NA2], [CH₂(8-Br-NA2)], [CH₂CH₂(8-Br-NA2)], [CH₂CH₂CH₂(8-Br-NA2)], [CH₂CH₂OPh], [CH₂CH₂OCH₂Ph], [CH₂CH₂CH₂OPh], [CH₂CH₂CH₂OCH₂Ph], [CH₂CH₂CH₂CH₂OPh], [CH₂CH₂CH₂CH₂OCH₂Ph], [CH₂CH₂CH₂CH₂CH₂OPh], [CH₂CH₂CH₂CH₂CH₂OCH₂Ph], [CH₂CH₂O(NA2)], [CH₂CH₂OCH₂(NA2)], [CH₂CH₂CH₂O(NA2)], [CH₂CH₂CH₂OCH₂(NA2)], [CH₂CH₂CH₂CH₂O(NA2)], [CH₂CH₂CH₂CH₂OCH₂(NA2)], [CH₂CH₂CH₂CH₂CH₂O(NA2)], [CH₂CH₂CH₂CH₂CH₂OCH₂(NA2)], [CH₂CH₂(IN1)], [CH₂CH₂(IN2)], [CH₂CH₂(Py2)], [CH₂CH₂(Qun2)], [CH₂CH₂(Fur2)], [CH₂CH₂(Thi2)], [CH₂CH₂(BF5)], [CH₂CH₂(BF2)], [CH₂CH₂(BT5)], [CH₂CH₂(BT2)], [CH₂CH₂(BDXO5)], [CH₂CH₂(BDXA6)], [CH₂(3Cy)], [CH₂CH₂(3Cy)], [CH₂(5Cy)], [CH₂CH₂(5Cy)], [CH₂(8Cy)], [CH₂CH₂(8Cy)], [CH₂CH₂(2,2-F₂-3Cy)], [CH₂CH₂(2-CN-3Cy)], [CH₂CH₂(2,2-F₂-BDXO5)], [CH₂CH₂(2,2-F₂-3Cy)], [IN1], [Py2], [Thi2], [3Cy], [5Cy], [CH₂TN].

The compound represented by formula (Y-5) wherein $U^1$ represents [CH₂CH₂CH₂(4-F-Ph)], represents the compound represented formula (Y-5) wherein $U^1$ represents 3-(4-fluorophenyl)propyl, which represents the compound represented by the following structure.

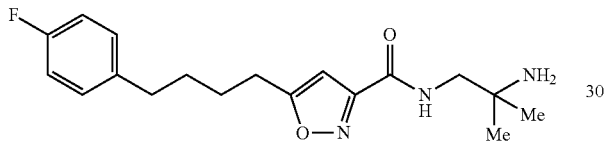

The amide compounds represented by formula (Y-20) to formula (Y-47) [wherein $U^2$ represents any group selected from the following Group (U-2)]]

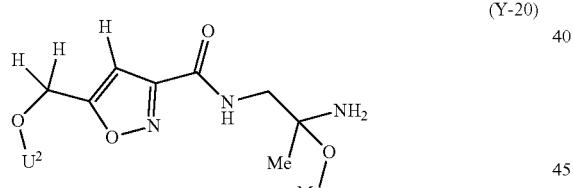 (Y-20)

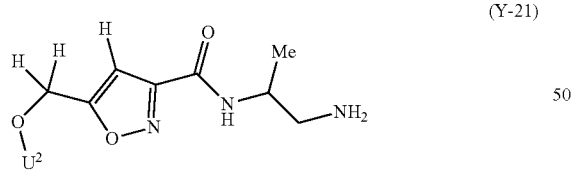 (Y-21)

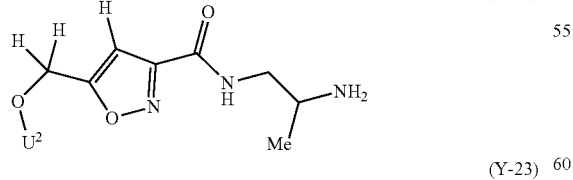 (Y-22)

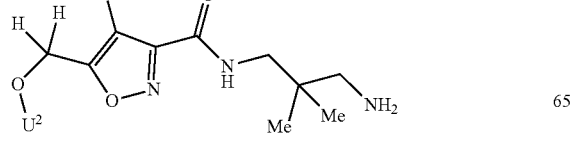 (Y-23)

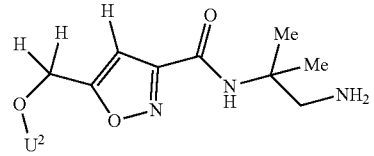 (Y-24)

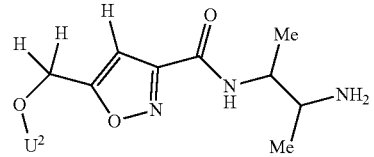 (Y-25)

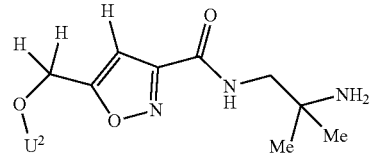 (Y-26)

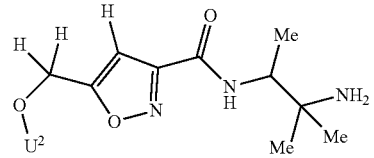 (Y-27)

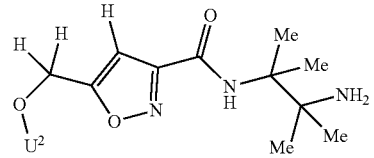 (Y-28)

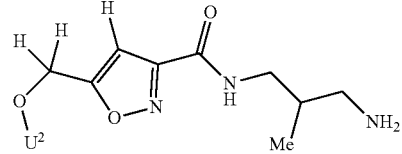 (Y-29)

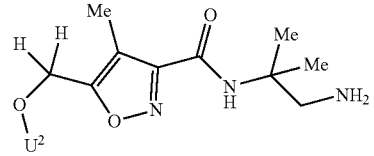 (Y-30)

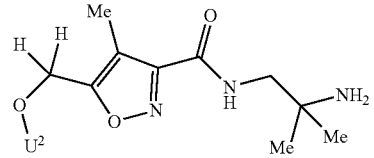 (Y-31)

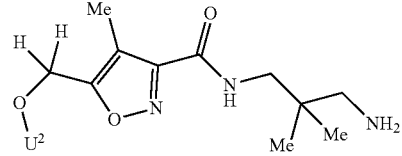 (Y-32)

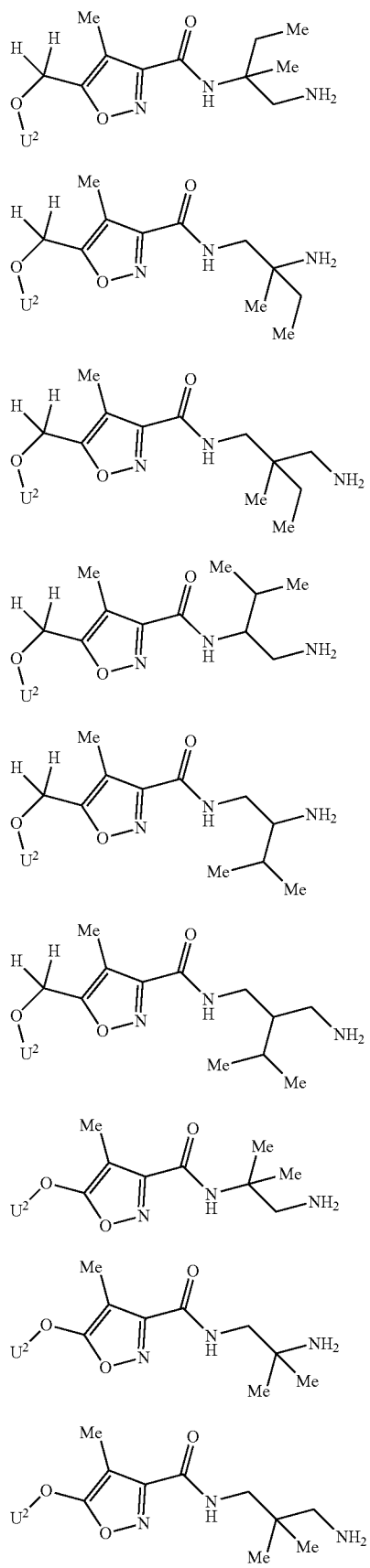
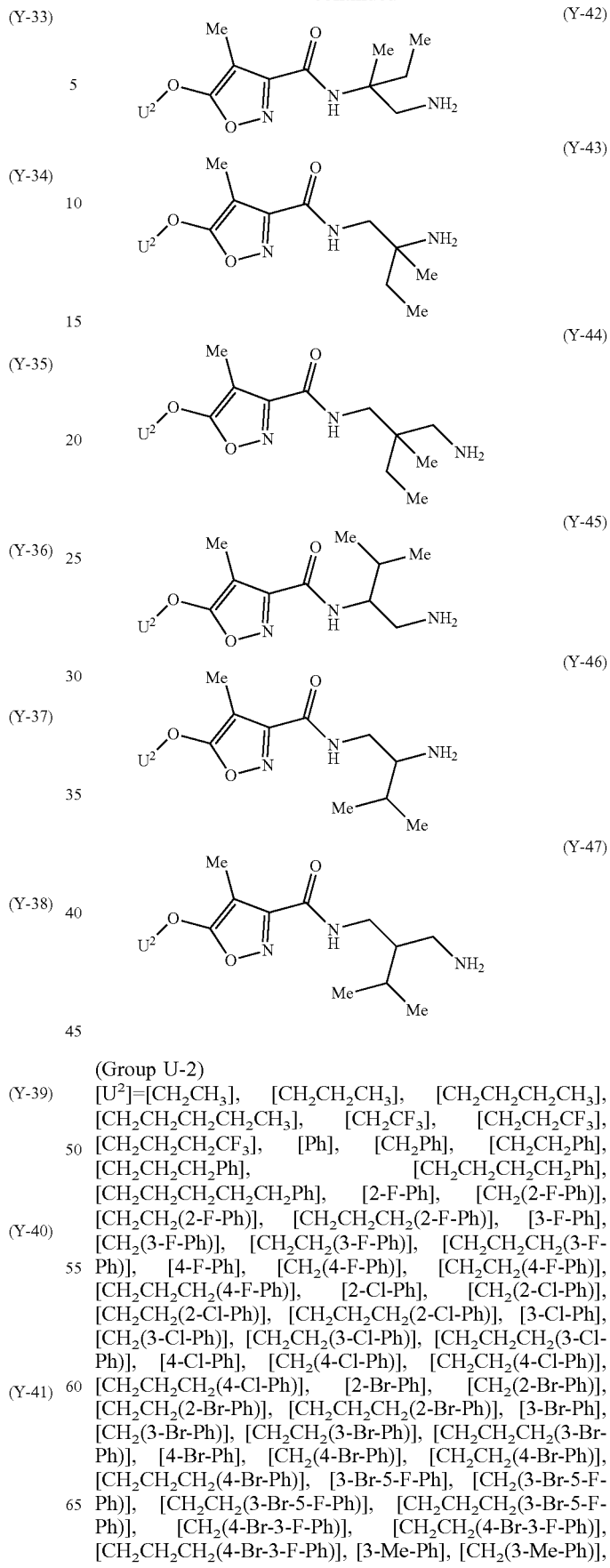

(Group U-2)
[U²]=[CH₂CH₃], [CH₂CH₂CH₃], [CH₂CH₂CH₂CH₃], [CH₂CH₂CH₂CH₂CH₃], [CH₂CF₃], [CH₂CH₂CF₃], [CH₂CH₂CH₂CF₃], [Ph], [CH₂Ph], [CH₂CH₂Ph], [CH₂CH₂CH₂Ph], [CH₂CH₂CH₂CH₂Ph], [CH₂CH₂CH₂CH₂CH₂Ph], [2-F-Ph], [CH₂(2-F-Ph)], [CH₂CH₂(2-F-Ph)], [CH₂CH₂CH₂(2-F-Ph)], [3-F-Ph], [CH₂(3-F-Ph)], [CH₂CH₂(3-F-Ph)], [CH₂CH₂CH₂(3-F-Ph)], [4-F-Ph], [CH₂(4-F-Ph)], [CH₂CH₂(4-F-Ph)], [CH₂CH₂CH₂(4-F-Ph)], [2-Cl-Ph], [CH₂(2-Cl-Ph)], [CH₂CH₂(2-Cl-Ph)], [CH₂CH₂CH₂(2-Cl-Ph)], [3-Cl-Ph], [CH₂(3-Cl-Ph)], [CH₂CH₂(3-Cl-Ph)], [CH₂CH₂CH₂(3-Cl-Ph)], [4-Cl-Ph], [CH₂(4-Cl-Ph)], [CH₂CH₂(4-Cl-Ph)], [CH₂CH₂CH₂(4-Cl-Ph)], [2-Br-Ph], [CH₂(2-Br-Ph)], [CH₂CH₂(2-Br-Ph)], [CH₂CH₂CH₂(2-Br-Ph)], [3-Br-Ph], [CH₂(3-Br-Ph)], [CH₂CH₂(3-Br-Ph)], [CH₂CH₂CH₂(3-Br-Ph)], [4-Br-Ph], [CH₂(4-Br-Ph)], [CH₂CH₂(4-Br-Ph)], [CH₂CH₂CH₂(4-Br-Ph)], [3-Br-5-F-Ph], [CH₂(3-Br-5-F-Ph)], [CH₂CH₂(3-Br-5-F-Ph)], [CH₂CH₂CH₂(3-Br-5-F-Ph)], [CH₂(4-Br-3-F-Ph)], [CH₂CH₂(4-Br-3-F-Ph)], [CH₂CH₂CH₂(4-Br-3-F-Ph)], [3-Me-Ph], [CH₂(3-Me-Ph)],

[CH₂CH₂(3-Me-Ph)], [CH₂CH₂CH₂(3-Me-Ph)], [2-CF₃-Ph], [CH₂(2-CF₃-Ph)], [CH₂CH₂(2-CF₃-Ph)], [CH₂CH₂CH₂(2-CF₃-Ph)], [3-CF₃-Ph], [CH₂(3-CF₃-Ph)], [CH₂CH₂(3-CF₃-Ph)], [CH₂CH₂CH₂(3-CF₃-Ph)], [4-CF₃-Ph], [CH₂(4-CF₃-Ph)], [CH₂CH₂(4-CF₃-Ph)], [CH₂CH₂CH₂(4-CF₃-Ph)], [3-OMe-Ph], [CH₂(3-OMe-Ph)], [CH₂CH₂(3-OMe-Ph)], [CH₂CH₂CH₂(3-OMe-Ph)], [4-OMe-Ph], [CH₂(4-OMe-Ph)], [CH₂CH₂(4-OMe-Ph)], [CH₂CH₂CH₂(4-OMe-Ph)], [2-OCF₃-Ph], [CH₂(2-OCF₃-Ph)], [CH₂CH₂(2-OCF₃-Ph)], [CH₂CH₂CH₂(2-OCF₃-Ph], [3-OCF₃-Ph], [CH₂(3-OCF₃-Ph)], [CH₂CH₂(3-OCF₃-Ph)], [CH₂CH₂CH₂(3-OCF₃-Ph)], [4-OCF₃-Ph], [CH₂(4-OCF₃-Ph)], [CH₂CH₂(4-OCF₃-Ph)], [CH₂CH₂CH₂(4-OCF₃-Ph)], [2-SCF₃-Ph], [CH₂(2-SCF₃-Ph)], [CH₂CH₂(2-SCF₃-Ph)], [CH₂CH₂CH₂(2-SCF₃-Ph)], [3-SCF₃-Ph], [CH₂(3-SCF₃-Ph)], [CH₂CH₂(3-SCF₃-Ph)], [CH₂CH₂CH₂(3-SCF₃-Ph)], [4-SCF₃-Ph], [CH₂(4-SCF₃-Ph)], [CH₂CH₂(4-SCF₃-Ph)], [CH₂CH₂CH₂(4-SCF₃-Ph)], [NA1], [CH₂(NA1)], [CH₂CH₂(NA1)], [CH₂CH₂CH₂(NA1)], [NA2], [CH₂(NA2)], [CH₂CH₂(NA2)], [CH₂CH₂CH₂(NA2)], [CH₂CH₂CH₂CH₂(NA2)], [CH₂CH₂CH₂CH₂CH₂(NA2)], [8-F-NA2], [CH₂(8-F-NA2)], [CH₂CH₂(8-F-NA2)], [CH₂CH₂CH₂(8-F-NA2)], [8-Cl-NA2], [CH₂(8-Cl-NA2)], [CH₂CH₂(8-Cl-NA2)], [CH₂CH₂CH₂(8-Cl-NA2)], [8-Br-NA2], [CH₂(8-Br-NA2)], [CH₂CH₂(8-Br-NA2)], [CH₂CH₂CH₂(8-Br-NA2)], [CH₂CH₂OPh], [CH₂CH₂O(NA2)], [CH₂(IN1)], [CH₂CH₂(IN2)], [CH₂(Py2)], [CH₂(Qun2)], [CH₂(Fur2)], [CH₂(Thi2)], [CH₂(BF5)], [CH₂(BF2)], [CH₂(BT5)], [CH₂(BT2)], [CH₂(BDXO5)], [CH₂(BDXA6)], [CH₂(3Cy)], [CH₂(5Cy)], [CH₂(8Cy)], [CH₂(2, 2-F₂-3CY)], [CH₂(2-CN-3 CY)], [CH₂(2,2-F₂-BDXO5)], [CH₂(2,2-F₂-3 Cy)], [Py2], [Thi2], [Fur2], [3Cy], [5Cy], [CH₂TN].

The compound represented by formula (Y-26) wherein U² represents [CH₂(3Cy)], represents the compound represented by formula (Y-26) wherein U² represents cyclopropylmethyl, which represents the compound represented by the following structure.

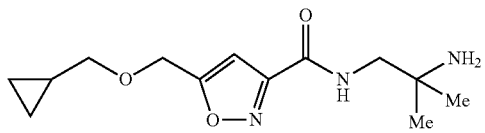 [SMILES: CC(C)(N)CNC(=O)c1cc(COCC2CC2)on1]

Next, the formulation examples of the Present compound are shown below. The "parts" represents "part by weight" unless otherwise specified.

Formulation Example 1

To 20 parts of any one of Present compound A, 65 parts of xylene, 7.5 parts of calcium dodecylbenzenesulfonate and 7.5 parts of nonylphenol ethoxylate are added, and the mixture is thoroughly mixed with stirring to obtain emulsifiable concentrates.

Formulation Example 2

To 40 parts of any one of Present compound A, 2.5 parts of calcium dodecylbenzenesulfonate and 2.5 parts of nonylphenol ethoxylate are added, and the mixture is thoroughly mixed, and 32 parts of hydrated silicon dioxide and 23 parts of 300-mesh diatomaceous earth are added thereto, followed by mixing with stirring by a mixer to obtain wettable powders.

Formulation Example 3

A mixture of 1.5 parts of any one of Present compound A, 1 part of synthetic hydrated silicon oxide, 2 parts of sodium lignin sulfonate, 30 parts of bentonite, and 65.5 parts of kaolin clay is thoroughly pulverized and mixed, and water is added thereto. The mixture is thoroughly kneaded, granulated by an extruding granulator, and then dried to obtain 1.5% granules.

Formulation Example 4

A mixture of 10 parts of any one of Present compound A, 10 parts of phenylxylylethane, and 0.5 parts of tolylene diisocyanate is mixed, and the resulting mixture is added to 20 parts of 10% aqueous solution of gum arabic, and the mixture is stirred with a homomixer to obtain an emulsion having an average particle diameter of 20 μm. To the emulsion, 2 parts of ethylene glycol is added, and the mixture is further stirred at 60° C. in a warm bath for 24 hours to obtain microcapsule slurry. Separately, 0.2 parts of xanthan gum and 1.0 part of aluminum magnesium silicate are dispersed into 56.3 parts of ion-exchanged water to obtain a thickener solution. Then, 42.5 parts of the above-mentioned microcapsule slurry and 57.5 parts of the above-mentioned thickener solution are mixed to obtain microcapsules Formulation Example 5

A mixture of 10 parts of any one of Present compound A and 10 parts of phenylxylylethane is mixed, and the resulting mixture is added to 20 parts of 20 parts of a 10% aqueous solution of polyethylene glycol, and the mixture is stirred by a homomixer to obtain an emulsion having an average particle diameter of 3 μm. Separately, 0.2 parts of xanthan gum and 1.0 part of aluminum magnesium silicate are dispersed into 58.8 parts of ion-exchanged water to obtain a thickener solution. Then, 40 parts of the above-mentioned emulsion solution and 60 parts of the above-mentioned thickener solution are mixed to obtain flowable formulations.

Formulation Example 6

To 5 parts of any one of Present compound A, 3 parts of synthetic hydrated silicon oxide, 0.3 parts of PAP, and 91.7 parts of talc (300 mesh) are added, and the mixture is mixed with stirring by a mixer to obtain dusts.

Formulation Example 7

Zero point one (0.1) parts of any one of Present compound A is added to 10 parts of isopropyl alcohol, and the mixture is mixed with 89.9 parts of kerosine to obtain oil solutions.

Formulation Example 8

A mixture of 1 part of any one of Present compound A, 5 parts of dichloromethane, and 34 parts of kerosine is mixed, and the mixture is filled into an aerosol container, and a valve portion is installed. Then, 60 parts of powder propellant (liquefied petroleum gas) is filled therein under pressure through the valve portion to obtain oil-based aerosol formulations.

Formulation Example 9

A mixture of 0.6 parts of any one of Present compound A, 5 parts of xylene, 3.4 parts of kerosine, and 1 part of ATOMOS (Registered trademark) 300 (emulsifier) is mixed. Then, the resulting mixture and 50 parts of water are filled into an aerosol container, and then 40 parts of powder propellant (liquefied propellant gas) is filled therein under pressure through a valve portion to obtain aqueous aerosol formulations.

Formulation Example 10

Zero point three (0.3) g of any one of Present Compound A is dissolved into 20 mL of acetone, and the resulting mixture is uniformly mixed while stirring with 99.7 g of a base material for incense stick (a base material obtained by mixing Tabu powder, Pyrethrum mark, and wooden powder at a ratio of 4:3:3). Then, 100 mL of water is added thereto, and the mixture is thoroughly kneaded, dried and molded to obtain insecticidal coils.

Formulation Example 11

To a mixture of 0.8 g of any one of Present compound A and 0.4 g of piperonyl butoxide, acetone is added so as to adjust the total volume of the mixture to 10 mL. Then, 0.5 mL of this solution is uniformly impregnated into a base material for an insecticidal mat for electric heating (a plate obtained by hardening fibrils of a mixture of cotton linters and pulp) having a size of 2.5 cm×1.5 cm and a thickness of 0.3 cm to obtain insecticidal mats for electric heating.

Formulation Example 12

Three (3) parts of any one of Present compound A is added 97 parts of kerosine to obtain liquid solutions. The resulting mixture is poured into a vessel made of vinyl chloride. A liquid absorptive core whose upper part can be heated by a heater (an inorganic pulverized powder is hardened with a binder and sintered) is inserted there into to obtain parts to be used for a liquid absorptive core type thermal transpiring apparatus.

Formulation Example 13

One hundred (100) mg of any one of Present compound A is dissolved into an appropriate amount of acetone, and the resulting mixture is impregnated into a porous ceramic plate having a size of 4.0 cm×4.0 cm, and a thickness of 1.2 cm to obtain thermal fumigants.

Formulation Example 14

One hundred (100) μg of any one of Present compound A is dissolved into an appropriate amount of acetone, and the resulting mixture is uniformly applied to filter paper having a size of 2 cm×2 cm and a thickness of 0.3 mm, and acetone is air-dried, and thus volatile agents for using at room temperature are obtained.

Formulation Example 15

A mixture of 10 parts of any one of Present compound A, and 35 parts of a mixture of a polyoxyethylene alkyl ether sulfate ammonium salt and white carbon (weight ratio of 1:1), and 55 parts of water, is mixed, and the resulting mixture is then finely ground by a wet grinding method to obtain each flowable formulation.

Next, an efficacy of Present compound on controlling harmful arthropod is shown as Test Example.

Test Example 1

Each of formulations that were prepared in Formulation Example 7 containing Present compounds (1), (2), (3), (4), (5), (6), (16), (18), (21), (22), (33), (34) and (35) was diluted with a mixed solution of isopropyl alcohol/kerosine=1/9 so as to make a concentration of each of the compound 0.5% w/v, to obtain a diluted solution containing Present compounds (1), (2), (3), (4), (5), (6), (16), (18), (21), (22), (33), (34) and (35), respectively.

Ten (10) adult female common house mosquitoes (*Culex pipers pallens*) were released in a polyethylene cup (bottom diameter 10.6 cm), and the polyethylene cup was covered with 16-mesh nylon gauze. The polyethylene cup was set at the inside bottom of a test chamber (bottom face: 46 cm×46 cm, height: 70 cm). Each 0.5 mL of the above-mentioned diluted solutions was sprayed using a spray gun (at a pressure of 0.4 kg/cm$^2$) from 30 cm higher than the upper face of the polyethylene cup. Immediately after the spraying, the cup was pulled out from the test chamber. After 2 minutes, 5 minutes, and 15 minutes, the number of knocked-down insects (the number of insects in a knocked-down state after the respective prescribed time was elapsed) was counted, and a knock-down ratio was determined by the following equation.

Knocked-down ratio (%)=(Number of knocked-down insects/Number of test insects)×100

As a result, when Present compounds (1), (2), (3), (4), (5), (6), (16), (18), (21), (22), (33), (34) and (35), respectively, was used, every of the knocked-down ratio showed 80° or more.

Test Example 2

Each of the formulations that were prepared in Formulation Example 15 containing Present compounds (1), (2), (3) and (4) was diluted with water so as to make a concentration of each of the compound 500 ppm, to obtain a diluted solution containing Present compounds (1), (2), (3) and (4), respectively. The above-mentioned diluted solutions were added to 100 mL of ion-exchanged water (Concentrations of Present compounds were 3.5 ppm). Thirty (30) heads of common house mosquitoes (*Culex pipens pallens*) at the last instar larval stages were released into the resulting diluted solutions having the concentration of 3.5 ppm, and after 1 day, the life and death of the insects were examined, and the mortality of insects was calculated by the following equation.

Mortality (%)=(Number of the dead insects/Number of test insects)×100

As a result, the treated group that was treated with Present compounds (1), (2), (3) and (4), respectively showed 91% or more as the mortality.

Test Example 3

Each of the formulations that were prepared in Formulation Example 15 containing Present compounds (1) and (2) was diluted with water so as to make a concentration of each of the compound 500 ppm, to obtain a diluted solution containing Present compounds (1) and (2), respectively.

The inside bottom of the polyethylene cup having 5.5 cm of diameter was matted with the same size of a filter paper, and 0.7 ml of the diluted solution was added dropwise on the filter paper, and 30 mg of sucrose as a bait was placed in the polyethylene cup uniformly. Ten (10) heads of female adult housefly (*Muscadomestica*) were released into the polyethylene cup, and the cup was covered with the lid. After 24 hours, the life and death of housefly was examined and the mortality of insects was calculated by the following equation.

Mortality (%)=(Number of the dead insects/Number of tested insects)×100

As a result, Present compounds (1) and (2), respectively showed 80% or more as the mortality.

Test Example 4

Each of the formulations that were prepared in Formulation Example 7 containing Present compounds (1), (2), (3), (5), (7), (8), (11), (12), (13), (14), (15), (17), (19), (20), (24), and (36) was diluted with a mixed solution of isopropyl alcohol/kerosin=1/9 so as to make a concentration of each of the compound 0.00625% w/v, to obtain a diluted solution containing Present compounds (1), (2), (3), (5), (7), (8), (11), (12), (13), (14), (15), (17), (19), (20), (24), and (36), respectively.

Ten (10) adult common house mosquitoes (*Culex pipens pallens*) were released in a polyethylene cup (bottom diameter 10.6 cm), and the polyethylene cup was covered with 16-mesh nylon gauze. The polyethylene cup was set at the inside bottom of a test chamber (bottom face: 46 cm×46 cm, height: 70 cm). Each 0.5 mL of the above-mentioned diluted solutions was sprayed using a spray gun (at a pressure of 0.4 kg/cm$^2$) from 30 cm higher than the upper face of the polyethylene cup. Immediately after the spraying, the cup was pulled out from the test chamber. After 2 minutes, 5 minutes, and 15 minutes, the number of knocked-down insects (the number of insects in a knocked-down state after the respective prescribed time was elapsed) was counted, and a knocked-down ratio was determined by the following equation.

Knocked-down ratio (%)=(Number of knocked-down insects/Number of test insects)×100

As a result, when Present compounds (1), (2), (3), (5), (7), (8), (11), (12), (13), (14), (15), (17), (19), (20), (24), and (36), respectively, was used, every of the knocked-down ratio showed 80% or more.

Test Example 5

Each of the formulations that were prepared in Formulation Example 7 containing Present compounds (7), (8), (9), (10), (11), (12), (13), (15), (17), (19), (20), (23), (24), (26), (27), (29), (30), (31), (32), and (36), respectively was diluted with a mixed solution of isopropyl alcohol/kerosin=1/9 so as to make a concentration of each of the compound 0.5% w/v, to obtain a diluted solution containing Present compounds (7), (8), (9), (10), (11), (12), (13), (15), (17), (19), (20), (23), (24), (26), (27), (29), (30), (31), (32), and (36), respectively.

Ten (10) adult German cockroaches (*Blattella germanica*, 5 males and 5 females) were released in a test container (diameter 8.75 cm, height 7.5 cm, the bottom face was made of 16 mesh metallic wire), the inner face on which butter was applied, and the container was set at the bottom of a test chamber (bottom face: 46 cm×46 cm, height: 70 cm). Each 1.5 mL of the diluted solution was sprayed using a spray gun (at a pressure of 0.42 kg/cm$^2$) from 60 cm higher than the upper face of the container. Immediately after the spraying, the cup was pulled out from the test chamber. After 2 minutes, 5 minutes, and 15 minutes, the number of knocked-down insects (the number of a knocked-down state after the respective prescribed time was elapsed) was counted, and a knock-down ratio was determined by the following equation.

Knocked-down ratio (%)=(Number of knocked-down insects/Number of test insects)×100

As a result, when Present compounds (7), (8), (9), (10), (11), (12), (13), (15), (17), (19), (20), (23), (24), (26), (27), (29), (30), (31), (32), and (36), respectively, was used, every of the knocked-down ratio showed 80% or more.

Test Example 6

Each of the formulations that are prepared in Formulation Example 15 containing each of Present compounds is diluted with water so as to prepare a diluted solution containing a prescribed concentration of the present compound.

The inside bottom of the polyethylene cup having 5.5 cm of diameter is matted with the same size of a filter paper, and 0.7 ml of the diluted solution is added dropwise on the filter paper, and 30 mg of sucrose as a bait is placed in the polyethylene cup uniformly. Ten (10) heads of female adult housefly (*Muscadomestica*) are released into the polyethylene cup, and the cup is covered with the lid. After 24 hours, the life and death of housefly is examined and the mortality of insects is calculated by the following equation.

Mortality (%)=(Number of the dead insects/Number of tested insects)×100

Test Example 7

Each of the formulations that are prepared in Formulation Example 15 containing each of Present compounds is diluted with water so as to prepare a diluted solution containing a prescribed concentration of the present compound.

The inside bottom of the polyethylene cup having 5.5 cm of diameter is matted with the same size of a filter paper, and 0.7 ml of the diluted solution is added dropwise on the filter paper, and 30 mg of sucrose as a bait is placed in the polyethylene cup uniformly. Two (2) heads of adult male German cockroaches (*Blattella germanica*, 5 males and 5 females) are released into the polyethylene cup, and the cup is covered with the lid. After 6 days, the life and death of German cockroach is examined and the mortality of insects is calculated by the following equation.

Mortality (%)=(Number of the dead insects/Number of tested insects)×100

Test Example 8

Each of Present compounds is made to a formulation according to the similar method to those described in Formulation Example 15, and thereto is added water containing 0.03 v/v % of a spreader to prepare a diluted solution containing a prescribed concentration of the present compound.

Cucumber (*Cucumis sativus*) seedling (on the developmental stage of the second true leaf) is planted in a plastic cup and approximately 30 heads of cotton aphid (*Aphis gossypii*) (all stages of life) are released onto the leaves of the cucumber. After 1 day, the diluted solutions are sprayed into the seedling in a ratio of 10 mL/seedling. After 5 days, the number of the surviving insects is examined and the controlling value is calculated by the following equation.

Controlling value (%)={1−(Cb×Tai)/(Cai×Tb)}×100 wherein the symbols in the formula represent the following descriptions.
Cb: Number of the test insects in untreated group;
Cai: Number of the surviving insects at the time of the investigation in untreated group;
Tb: Number of the test insects in treated group;
Tai: Number of the surviving insects at the time of the investigation in treated group;
Here the "untreated group" represents a group where the similar treatment procedure to that of the treated group except not using the test compound is done.

Test Example 9

Each of Present compounds is made to a formulation according to the similar method to those described in Formulation Example 15, and thereto is added water containing 0.03 v/v % of a spreader to prepare a diluted solution containing a prescribed concentration of the present compound.
Rice (*Oryza sativa*) seedling (on the developmental stage of the second true leaf) is planted in a plastic cup, and the diluted solutions are sprayed into the seedling in a ratio of 10 mL/seedling. Thereafter, 20 heads of 3rd instar larvae of brown planthopper (*Nilaparvata lugens*) are released onto the rice leaves. After 6 days, the mortality is calculated by the following equation.

Mortality (%)={1−the number of the surviving insects/20}×100

Test Example 10

Each of Present compounds is made to a formulation according to the similar method to those described in Formulation Example 15, and thereto is added water to prepare a diluted solution containing a prescribed concentration of the present compound.
To the plastic cup, the diluted solution is added, and Rice (*Oryza sativa*) seedling (on the developmental stage of the second true leaf) that is planted in a plastic cup is installed.
After 7 days, 20 heads of 3rd instar larvae of brown planthopper (*Nilaparvata lugens*) are released. After additional 6 days, the number of the surviving insects is examined, and the mortality is calculated by the following equation.

Test Example 11

Each of Present compounds is made to a formulation according to the similar method to those described in Formulation Example 15, and thereto is added water to prepare a diluted solution containing a prescribed concentration of the present compound.
In the plastic cup, 7.7 g of artificial diet (Insecta LF, manufactured by NOSAN CORPORATION) is placed, and 2 mL of the diluted solution is irrigated thereto. Five (5) heads of fourth instar larvae of tobacco cutworm (*Spodoptera litura*) are released onto the artificial diet, and the plastic cup is covered with a lid. After 5 days, the number of the surviving insects is examined, and the mortality is calculated by the following equation.

Mortality (%)={1−the number of the surviving insects/5}×100

Test Example 12

Present compounds are made to a formulation according to a similar method to those described in Formulation Example 15, and thereto is added water containing 0.03 v/v % of a spreader to prepare a diluted solution containing a prescribed concentration of Present compound.
The diluted solutions are sprayed into the cabbage (*Brassicae oleracea*) seedling (on the development stage of the second to third true leaf) that is planted in the plastic cup in a ratio of 20 mL/seedling. Thereafter, the stem and leaf thereof is cut out and then is installed into the plastic cup that is covered with the filter paper. Five (5) heads of diamondback moth (*Plutella xylostella*) at the second instar larval stages is released into the cup, and the cup is covered with a lid. After 5 days, the surviving insects are counted, and the mortality of insects is calculated by the following equation.

Mortality (%)={1−the number of the surviving insects/5}×100

INDUSTRIAL APPLICABILITY

The control agent of the present invention has excellent efficacies on controlling harmful arthropods.

The invention claimed is:
1. An agent for controlling harmful arthropods, the agent comprising an inert carrier and an amide compound represented by formula (I):

$$Q-Y-\underset{m}{\underbrace{\begin{pmatrix} R^5 & R^6 \\ & \end{pmatrix}}}\underset{O-N}{\overset{R^2}{\diagdown}}\overset{O}{\underset{H}{\diagdown}}N\underset{R^9\ R^{10}}{\underbrace{\begin{pmatrix} R^{11}\ R^{12} \\ & \end{pmatrix}}_b}NH_2 \quad (I)$$

wherein:
$R^2$ represents a C1-C3 chain hydrocarbon group optionally substituted with one or more substituents selected from a group consisting of hydroxy group and halogen atom, a hydrogen atom, a halogen atom, a cyano group and a formyl group,
$R^9$ represents a C1-C4 alkyl group optionally substituted with one or more fluorine atoms or a C1-C4 alkoxy group optionally substituted with one or more fluorine atoms,
$R^{10}$ represents a C1-C4 alkyl group optionally substituted with one or more fluorine atoms, a C1-C4 alkoxy group optionally substituted with one or more fluorine atoms, or a hydrogen atom,
$R^{11}$ represents a C1-C4 alkyl group optionally substituted with one or more fluorine atoms, a C1-C4 alkoxy group optionally substituted with one or more fluorine atoms, or a hydrogen atom,
$R^{12}$ represents a C1-C4 alkyl group optionally substituted with one or more fluorine atoms, a C1-C4 alkoxy group optionally substituted with one or more fluorine atoms, or a hydrogen atom,
Y represents a single bond,
m is 0, and Q represents a 1-propyl, 1-butyl, 1-pentyl, 1-hexyl, 1-heptyl, or 1-octyl group,
each of a and b is 0, 1, 2, or 3, provided that the sum of a and b represents any one of an integer of 1 to 6.

* * * * *